(12) United States Patent
Wekell et al.

(10) Patent No.: US 8,956,292 B2
(45) Date of Patent: Feb. 17, 2015

(54) TRENDING DISPLAY OF PATIENT WELLNESS

(75) Inventors: William Wekell, Maple Valley, WA (US); Robert Boyer Koenig, Redmond, WA (US); Patricia Walters, Redmond, WA (US); Bob Steurer, Sammamish, WA (US); Vicki Childress, Redmond, WA (US); Diane S. Paine, Redmond, WA (US); Kim Apker, Bothell, WA (US); Kyril Feldman, Kirkland, WA (US); Al Roxin, Edmonds, WA (US)

(73) Assignee: Spacelabs Healthcare LLC, Snoqualmie, WA (US)

( * ) Notice: Subject to any disclaimer, the term of this patent is extended or adjusted under 35 U.S.C. 154(b) by 1808 days.

(21) Appl. No.: 12/114,689

(22) Filed: May 2, 2008

(65) Prior Publication Data

US 2009/0054743 A1    Feb. 26, 2009

Related U.S. Application Data

(63) Continuation-in-part of application No. 11/365,196, filed on Mar. 1, 2006, now Pat. No. 8,690,771.

(60) Provisional application No. 60/657,913, filed on Mar. 2, 2005.

(51) Int. Cl.
*A61B 5/00* (2006.01)
*A61B 5/0205* (2006.01)
*G06F 19/00* (2011.01)
(Continued)

(52) U.S. Cl.
CPC ........... *A61B 5/02055* (2013.01); *A61B 5/7275* (2013.01); *A61B 5/7435* (2013.01); *G06F 19/3406* (2013.01); *G06F 19/345* (2013.01); *G06F 19/3487* (2013.01); *A61B 5/002* (2013.01); *A61B 5/742* (2013.01); *A61B 5/7445* (2013.01); *A61B 5/743* (2013.01); *A61B 5/01* (2013.01); *A61B 5/02* (2013.01); *A61B 5/024* (2013.01); *A61B 5/0402* (2013.01);
(Continued)

(58) Field of Classification Search
None
See application file for complete search history.

(56) References Cited

U.S. PATENT DOCUMENTS 3,618,592 A   11/1971   Stewart
4,513,294 A    4/1985   Anderson et al.
(Continued)

FOREIGN PATENT DOCUMENTS

EP    1054338    11/2000
GB    2389290    12/2003
(Continued)

OTHER PUBLICATIONS

Supplementary European Search Report, Nov. 25, 2009, Spacelabs Medical/PCT/US2006/007269.
(Continued)

*Primary Examiner* — William Thomson
*Assistant Examiner* — Bobby Soriano
(74) *Attorney, Agent, or Firm* — Novel IP

(57) ABSTRACT

The present invention is a novel method of generating and representing the status of various physiological parameters that are monitored for patients during hospitalization. The system of present invention allows healthcare providers to easily view, at a glance, the status or trend of a patient or a plurality of patients as well as any changes in the parameter values.

18 Claims, 22 Drawing Sheets

(51) Int. Cl.
  *A61B 5/01* (2006.01)
  *A61B 5/02* (2006.01)
  *A61B 5/024* (2006.01)
  *A61B 5/0402* (2006.01)
  *A61B 5/08* (2006.01)
  *A61B 5/145* (2006.01)

(52) U.S. Cl.
  CPC .............. *A61B 5/0816* (2013.01); *A61B 5/145* (2013.01); *A61B 5/14532* (2013.01)
  USPC .......................................................... 600/301

(56) References Cited

U.S. PATENT DOCUMENTS

| | | | |
|---|---|---|---|
| 4,697,450 A | 10/1987 | Bachman et al. | |
| 4,869,253 A | 9/1989 | Craig, Jr. et al. | |
| 4,944,305 A | 7/1990 | Takatsu | |
| 5,197,480 A | 3/1993 | Gebhardt | |
| 5,262,944 A | 11/1993 | Weisner et al. | |
| 5,319,363 A * | 6/1994 | Welch et al. | 340/8.1 |
| 5,331,549 A * | 7/1994 | Crawford, Jr. | 600/513 |
| 5,339,826 A | 8/1994 | Schmidt et al. | |
| 5,419,332 A | 5/1995 | Sabbah et al. | |
| 5,438,983 A | 8/1995 | Falcone | |
| 5,584,291 A | 12/1996 | Vapola et al. | |
| 5,718,235 A | 2/1998 | Golosarsky et al. | |
| 5,724,025 A | 3/1998 | Tavori | |
| 5,724,985 A * | 3/1998 | Snell et al. | 600/510 |
| 5,749,367 A | 5/1998 | Gamlyn et al. | |
| 5,800,360 A | 9/1998 | Kisner et al. | |
| 5,956,013 A * | 9/1999 | Raj et al. | 345/208 |
| 5,975,081 A * | 11/1999 | Hood et al. | 128/845 |
| 6,024,089 A * | 2/2000 | Wallace et al. | 128/204.21 |
| 6,063,028 A | 5/2000 | Luciano | |
| 6,134,537 A | 10/2000 | Pao et al. | |
| 6,322,502 B1 | 11/2001 | Schoenberg et al. | |
| 6,347,310 B1 | 2/2002 | Passera | |
| 6,383,136 B1 | 5/2002 | Jordan | |
| 6,443,889 B1 | 9/2002 | Groth et al. | |
| 6,488,029 B1 * | 12/2002 | Hood et al. | 128/845 |
| 6,571,227 B1 | 5/2003 | Agrafiotis et al. | |
| 6,647,341 B1 | 11/2003 | Golub et al. | |
| 6,650,779 B2 | 11/2003 | Vachtesvanos et al. | |
| 6,692,258 B1 * | 2/2004 | Kurzweil et al. | 434/262 |
| 6,692,436 B1 * | 2/2004 | Bluth et al. | 600/300 |
| 6,699,187 B2 * | 3/2004 | Webb et al. | 600/300 |
| 6,702,754 B2 | 3/2004 | Ogura et al. | |
| 6,771,172 B1 | 8/2004 | Robinson et al. | |
| 6,824,539 B2 * | 11/2004 | Novak | 606/1 |
| 6,829,501 B2 * | 12/2004 | Nielsen et al. | 600/513 |
| 6,985,762 B2 * | 1/2006 | Brashears et al. | 600/323 |
| 7,031,857 B2 | 4/2006 | Tarassenko et al. | |
| 7,038,588 B2 * | 5/2006 | Boone et al. | 340/573.1 |
| 7,081,091 B2 | 7/2006 | Merrett et al. | |
| 7,117,438 B2 * | 10/2006 | Wallace et al. | 715/709 |
| 7,137,951 B2 * | 11/2006 | Pilarski | 600/300 |
| 7,267,666 B1 * | 9/2007 | Duchon et al. | 604/151 |
| 7,282,029 B1 * | 10/2007 | Poulsen et al. | 600/300 |
| 7,315,825 B2 | 1/2008 | Rosenfeld et al. | |
| 7,371,214 B2 | 5/2008 | Kouchi et al. | |
| 7,386,340 B2 * | 6/2008 | Schlegel et al. | 600/517 |
| 7,468,032 B2 * | 12/2008 | Stahmann et al. | 600/301 |
| 7,523,040 B2 * | 4/2009 | Kirchhoff et al. | 705/2 |
| 7,756,722 B2 * | 7/2010 | Levine et al. | 705/2 |
| 7,945,452 B2 * | 5/2011 | Fathallah et al. | 705/2 |
| 2001/0027791 A1 * | 10/2001 | Wallace et al. | 128/204.21 |
| 2002/0026941 A1 * | 3/2002 | Biondi et al. | 128/204.21 |
| 2002/0161291 A1 * | 10/2002 | Kianl et al. | 600/324 |
| 2002/0193679 A1 * | 12/2002 | Malave et al. | 600/407 |
| 2002/0196141 A1 * | 12/2002 | Boone et al. | 340/540 |
| 2003/0028118 A1 * | 2/2003 | Dupree et al. | 600/509 |
| 2003/0037786 A1 * | 2/2003 | Biondi et al. | 128/204.21 |
| 2003/0114836 A1 * | 6/2003 | Estes et al. | 604/890.1 |
| 2003/0117296 A1 | 6/2003 | Seely | |
| 2003/0120164 A1 * | 6/2003 | Nielsen et al. | 600/513 |
| 2003/0145854 A1 * | 8/2003 | Hickle | 128/204.18 |
| 2003/0216621 A1 * | 11/2003 | Alpert et al. | 600/300 |
| 2003/0233129 A1 * | 12/2003 | Matos | 607/5 |
| 2004/0024303 A1 * | 2/2004 | Banks et al. | 600/407 |
| 2004/0032426 A1 | 2/2004 | Rutledge et al. | |
| 2004/0054261 A1 | 3/2004 | Kamataki et al. | |
| 2004/0054295 A1 * | 3/2004 | Ramseth | 600/509 |
| 2004/0102687 A1 * | 5/2004 | Brashears et al. | 600/323 |
| 2004/0103001 A1 | 5/2004 | Mazar | |
| 2004/0118404 A1 * | 6/2004 | Wallace et al. | 128/205.23 |
| 2004/0153257 A1 | 8/2004 | Munk | |
| 2004/0172222 A1 * | 9/2004 | Simpson et al. | 702/189 |
| 2004/0186357 A1 * | 9/2004 | Soderberg et al. | 600/300 |
| 2004/0236192 A1 * | 11/2004 | Necola Shehada et al. | 600/301 |
| 2005/0010165 A1 * | 1/2005 | Hickle | 604/66 |
| 2005/0038332 A1 * | 2/2005 | Saidara et al. | 600/347 |
| 2005/0054920 A1 * | 3/2005 | Washburn et al. | 600/437 |
| 2005/0113650 A1 * | 5/2005 | Pacione et al. | 600/300 |
| 2005/0124866 A1 * | 6/2005 | Elaz et al. | 600/301 |
| 2007/0176931 A1 * | 8/2007 | Tivig et al. | 345/440 |

FOREIGN PATENT DOCUMENTS

| | | |
|---|---|---|
| JP | 07-163527 | 6/1995 |
| JP | 2003210422 | 7/2003 |
| WO | WO 03/091841 | 11/2003 |
| WO | WO 03/102850 | 12/2003 |

OTHER PUBLICATIONS

PCT Report on Patentability PCT/US2006/007269, Mar. 2006, Spacelabs Medical.

Schoenberg, Roy, MD; Sands, Daniel Z., MD MPH; Safran, Charles, MD; Center for Clinical Computing, Beth Israel Deaconess Medical Center, Harvard Medical School, "Making ICU Alarms Meaningful: a comparison of traditional vs. trend-based algorithms" (AMIA '99 Annual Symposium), 1999, pp. 1-5.

* cited by examiner

FIG. 3

TRENDING DISPLAY OF PATIENT WELLNESS

CROSS-REFERENCE TO RELATED APPLICATIONS

The present application is a continuation-in-part of U.S. patent application Ser. No. 11/365,196, filed on Mar. 1, 2006, now U.S. Pat. No. 8,690,771 and entitled "Trending Display of Patient Wellness", which relies on U.S. Provisional Patent Application No. 60/657,913 filed on Mar. 2, 2005, entitled "Continuous Trending Display of Parameter Status".

FIELD OF THE INVENTION

The present invention relates generally to the field of systems and methods for monitoring physiological parameters of patients and, more particularly, to improved methods and apparatuses for displaying information related to such monitored physiological parameters. More specifically, the present invention relates to improved methods and apparatuses for aggregating, displaying, and manipulating the display of information related to monitored physiological parameters. Still more specifically, the present invention relates to methods of and apparatuses for searching for and displaying retrospective and prospective information related to monitored physiological parameters.

BACKGROUND OF THE INVENTION

Patient monitoring systems are commonly used in hospitals, such as in intensive care units (ICUs), for monitoring patient status and condition. Conventional patient monitoring systems typically include a bedside monitor having one or more sensors attached to the patient, for sensing parameters such as ECG, blood pressure, blood oxygen, blood glucose and temperature. The output from the sensors is sent to a system processor, which subsequently processes the measured values. These values may then be displayed on a video display screen or stored for later analysis. Data representing the measured physiological parameters is typically displayed as waveforms and/or numerical values.

Conventional patient monitoring systems are also capable of handling critical patient events or alarm conditions. For example, when the value of one of the physiological parameters being monitored exceeds a predetermined threshold value and/or meets predetermined alarm criteria, an alarm is activated by the bedside monitor and subsequently transmitted to a central monitoring station. The alarm can be annunciated at the central station in various ways, such as by highlighting relevant parameter information. An audible alarm is also typically generated at the central station.

In any information intensive or demanding medical environment, such as an intensive care unit, it is important to present the information on the display screen of a patient monitoring system in a clear and unambiguous manner. However, conventional patient monitoring systems are limited in their ability to present a comparison or evaluation of changing patient diagnostic variables. Although the conventional systems are useful in accumulating much useful data, accessing the data is oftentimes difficult and time-consuming.

Several patient monitoring systems have been disclosed in the prior art as highlighting critical patient events and alarm conditions. For example, U.S. Pat. No. 5,438,983, assigned to Koninklijke Philips Electronics, discloses "a patient monitoring system comprising: a sensor for measuring values representative of a physiological parameter; and a processor coupled to said sensor for processing said parameter values measured by said sensor, said processor comprising: means for determining whether said parameter values are within safe zone limits; means for initiating calculation of a trend vector when said parameter values go outside said safe zone limits, said trend vector being a function of changes in said parameter values and time; means for comparing said trend vector with an alarm limit function; and means for issuing an alarm when said trend vector exceeds said alarm limit function".

Prior art patient monitoring systems also include sensor systems that provide output signals indicative of normal, above normal or below normal sensed conditions. The signals may be used to monitor a condition and may be combined so that specific combinations of abnormal signals provide an indication of the condition of the patient. Although the prior art systems attempt to simultaneously communicate large amounts of patient data and information, these systems are lacking in that they do not provide the physician or clinician with efficient and effective means for quickly analyzing data in an information-rich environment.

In addition, with current patient monitoring systems, individual health parameters are typically seen as individual data elements. Clinicians look at each parameter separately to assess the composite trends of the status of the patient. Thus, it is often a time-consuming challenge for health care providers to accurately assess multiple parameters in context, thus resulting in errors or missed data, and further resulting in poor decisions regarding patient status.

What is therefore needed are methods, systems and apparatuses for monitoring of patient physiological parameters that facilitate the assessment of patient status and patient health on a unified display.

What is also needed is an improved method and apparatus for aggregating, displaying, and manipulating the display of information related to monitored physiological parameters.

What is also needed is a patient monitoring device that is able to continuously present the status of at least one measured parameter in a clear and concise manner, thus aiding healthcare providers in making decisions and drawing conclusions on patient wellness despite being confronted by substantial amounts of information in stressful environments such as an intensive care unit.

What is also needed is a patient monitoring device for recognizing data from a plurality of parameters and presenting the data on a unified display that can be manipulated and customized.

What is also needed is a patient monitoring device that is able to continuously present the status of a plurality of measured parameters in a clear and concise manner, thus aiding healthcare providers in making decisions and drawing conclusions on patient status.

Furthermore, what is needed is a patient monitoring system in which alarm conditions are clearly presented on the display screen of the patient monitoring system, such that a life-threatening patient condition can be differentiated from other, less serious alarms or with alarms that have already been acknowledged.

Additionally, what is needed is a patient monitoring system in which events are visually presented in a simple, facile manner that provides for rapid sorting of clinical data for quick access to relevant comprehensive information.

SUMMARY OF THE INVENTION

The present invention is directed to a system for monitoring a plurality of physiological parameters of an individual using a plurality of physiological sensors. The system includes a processor in data communication with a memory, wherein the memory stores physiological parameter data obtained from the plurality of sensors and wherein the processor executes a plurality of instructions to generate an interactive user interface based upon physiological parameter data, said interactive user interface comprising a) a first region having a plurality of icons, wherein each icon graphically represents a selectable graphical user interface view, b) a second region having at least two alternative interfaces, wherein a first alternative interface comprises a customizable table of measured values of physiological parameters presented in accordance with a time of measurement and wherein a second alternative interface has a customizable graph of measured values of physiological parameters presented in accordance with a time of measurement, c) a third region having at least one interface, wherein the at least one interface comprises a customizable graph of at least one measured value of at least one physiological parameter, d) a fourth region comprising a timebar that can be used to customize the time period for display, and e) a display unit coupled to said processor for visually displaying said user interface in accordance with the executed plurality of instructions.

Optionally, the physiological parameters comprise at least one of heart rate, pulse rate, ECG, blood oxygen saturation level (SpO$_2$), respiratory rate, blood glucose level, blood pressure and body temperature. The first region further comprises a menu having at least one button. The button comprises a bedside icon, a waveform icon, an arrhythmia icon, an alarms icon, a saved events icon, a 12-lead icon, a trends icon, or a print jobs icon. The first region further comprises a patient name area. The second region has a third alternative interface, wherein the third alternative interface is used for defining search parameters. The second region has a fourth alternative interface, wherein the fourth alternative interface is used for displaying defined search parameter data. The second region has a fifth alternative interface, wherein the fifth alternative interface is used for displaying banded graphs based on measured parameter data. The customizable graph presents, along a unified timeline, measured values for more than one physiological parameter.

In another embodiment, the present invention is directed to a method for monitoring a plurality of physiological parameters of an individual using a plurality of physiological sensors, including receiving data on physiological parameters, processing data on physiological parameters to form a user interface, where the user interface comprises a first region having a plurality of icons, wherein each icon graphically represents a selectable graphical user interface view, a second region having at least two alternative interfaces, wherein a first alternative interface comprises a customizable table of measured values of physiological parameters presented in accordance with a time of measurement and wherein a second alternative interface has a customizable graph of measured values of physiological parameters presented in accordance with a time of measurement, a third region having at least one interface, wherein the at least one interface comprises a customizable graph of at least one measured value of at least one physiological parameter, a fourth region comprising a timebar that can be used to customize the time period for display, and visually displaying the user interface.

Optionally, the physiological parameters comprise at least one of heart rate, pulse rate, ECG, blood oxygen saturation level (SpO$_2$), respiratory rate, blood glucose level, blood pressure and body temperature. The method of claim 10 wherein said first region further comprises a menu having at least one button. The at least one button comprises at least one of a bedside icon, a waveform icon, an arrhythmia icon, an alarms icon, a saved events icon, a 12-lead icon, a trends icon, or a print jobs icon. The first region further comprises a patient name area. The second region has a third alternative interface, wherein the third alternative interface is used for defining search parameters. The second region has a fourth alternative interface, wherein the fourth alternative interface is used for displaying defined search parameter data. The second region has a fifth alternative interface, wherein the fifth alternative interface is used for displaying banded graphs based on measured parameter data. The customizable graph presents, along a unified timeline, measured values for more than one physiological parameter.

The aforementioned and other embodiments of the present invention shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein:

FIG. 3 is an illustration of another embodiment of a central station patient information display of the present invention;

DETAILED DESCRIPTION OF THE INVENTION

Figure 1:
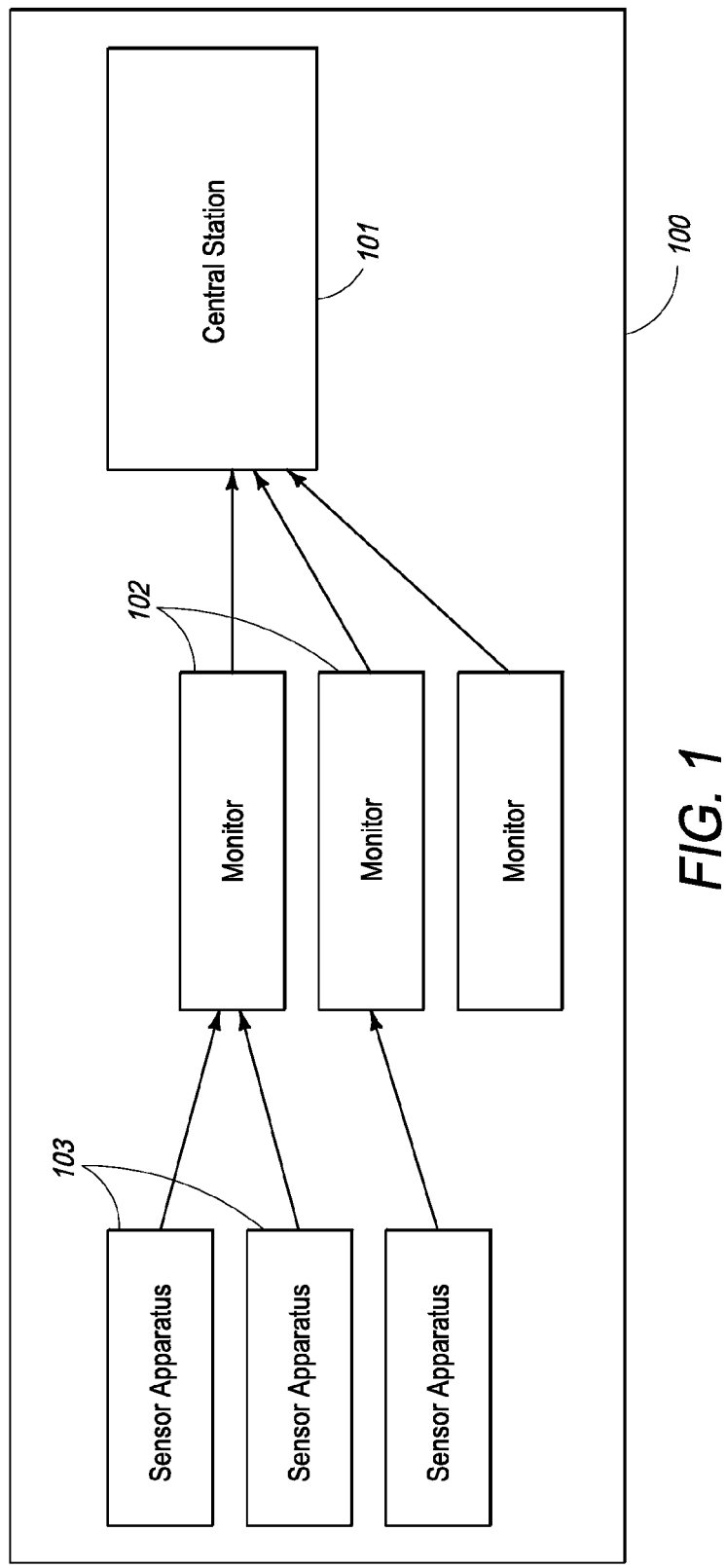
FIG. 1 is a diagrammatic illustration of one embodiment of a patient monitoring apparatus as used in the present invention.

The present invention is directed towards medical systems for monitoring physiological parameters of patients and, more particularly, to improved methods and apparatuses for displaying information related to monitored physiological parameters.

More specifically, the present invention is directed towards methods, systems and apparatuses for monitoring of patient physiological parameters that facilitate in the assessment of patient status and wellness.

Still more specifically, the present invention is directed towards improved methods and apparatuses for displaying patient wellness status, both by individual parameter trending and by calculating an overall wellness indicator.

In addition, the present invention is directed towards a method of generating and representing the status of at least one physiological parameter of a patient and displaying the status on the display portion of a medical system for monitoring physiological parameters of a patient.

In addition, the present invention is directed towards a method of generating, representing, and calculating the status of a plurality of physiological parameters of a patient and displaying the status on the display portion of a medical system for monitoring physiological parameters of a patient.

In addition, the present invention is directed towards a patient monitoring system in which a clinician is provided a defined rules-based view that will assist in accurate assessment of multiple parameters in a unified context and further, the overall wellness status of the patient.

In addition, the patient monitoring system of the present invention is able to continuously present the status of measured physiological parameters in a clear and concise manner. Thus, the present invention is also directed towards a patient monitoring system in which patient status with respect to overall wellness or individual parameter wellness are clearly presented on the display screen of the patient monitoring system, such that a life-threatening patient condition can be differentiated from other, less serious alarms or with alarms that have already been acknowledged.

In one embodiment, the overall wellness status of the patient represents an indication of a calculated composite of multiple physiological parameters.

In one embodiment, the system of the present invention enables healthcare providers to view, at a glance, the overall wellness status of at least one of a plurality of patients.

In one embodiment of the present invention, the system comprises both a visual retrospective and visual prospective trending display that provides a summary of a patient's overall wellness status within a predefined time period by combining the values of a user-defined group of data elements, including but not limited to physiological parameters, weight, age, and other calculations according to a rules-based engine algorithm. The user can thus configure the rules of the visual trending display by changing the individual parameters hard ceiling values, slope, timing, and calculations.

In one embodiment, the wellness status of a patient is represented on a display as a horizontal trend bar.

In one embodiment, the system of the present invention enables healthcare providers to view, at a glance, individual parameter wellness status of at least one patient. Optionally, the healthcare provider is able to view any changes in the individual parameter values.

In one embodiment, the individual parameter wellness status of the patient represents an indication of changes of at least one individual parameter value for a particular patient. In one embodiment, the indication of changes of at least one individual parameter value is based upon pre-determined threshold values.

In one embodiment, the individual parameter wellness status of a patient is represented on a display as a vertical trend bar. In one embodiment, the present invention comprises applying a distinctive color or shape to a portion of an individual patient parameter zone representing the status of an individual parameter. For example, with vertically-displayed parameter zones, the colored and/or shaped areas of the parameter zone visually comprise a vertical color light bar in one construction.

In one embodiment, the trend bar employs multiple colors and blends of multiple colors, such as but not limited to green, yellow and red to indicate levels and changes in the patient's retrospective status and allow composite views of the data over time.

In one embodiment, the present invention further comprises a predictive indicator. Preferably, the predictive indicator is an icon that displays a color indicator of the prospective trend for the future based upon configurable predictive rules. The color of the indicator is chosen as one that is distinct, such as, but not limited to green, yellow, and red. The trending indicators themselves are thus embodied in both hardware and/or software implementations.

In one embodiment, the trend bar is always visible; thus, a clinician can easily view simple trending information at a glance. The trend bar also serves as a "hot-link" to further display the data in more detail, including a miniature parameter trend display. The light bar trending is preferably user-defined for the density of the trend information as well as the duration of the data included. A corresponding rules-based engine takes into consideration user-defined upper and lower limits, baseline, slope, time, and calculations.

One of ordinary skill in the art would appreciate that the features described in the present application are enabled by source code, compiled into an executable application and executing on a computer. The computer can be any type of computing device, including a laptop, personal computer, personal digital assistant, cell phone, server, or specialized medical device. Additionally, the programmatic code can be compiled into a single application, executing on a single computer, or distributed among several different computers operating locally or remotely to each other.

Various modifications to the preferred embodiment will be readily apparent to those of ordinary skill in the art, and the disclosure set forth herein may be applicable to other embodiments and applications without departing from the spirit and scope of the present invention and the claims appended hereto. Thus, the present invention is not intended to be limited to the embodiments described, but is to be accorded the broadest scope consistent with the disclosure set forth herein.

FIG. 1 is a diagrammatic illustration of one embodiment of a patient monitoring apparatus as used in the present invention. Referring now to FIG. 1, in one embodiment of the present invention, patient monitoring system 100 comprises central monitoring station 101 and at least one monitor 102, which is preferably located at a patient bedside. In one embodiment, central station 101 is located at a nursing station or similar centrally located hospital staff location. As described in greater detail below, selected patient information received at central station 101 from at least one monitor 102 is presented on a video display (not shown) attached to the central station.

In one embodiment, each monitor 102 communicates with sensor apparatus 103, which further comprises at least one sensor (not shown). The sensor is attached to the patient (not shown) and is used to record various physiological parameters of the patient, such as but not limited to heart rate, ECG, invasive blood pressure, non-invasive blood pressure, body temperature (oral, rectal, and tympanic), respiration, end tidal carbon dioxide, oxygen, cardiac output, $SPO_2$, $SVO_2$, and various anesthesia gases.

In one embodiment, the at least one sensor obtains a measurement of at least one physiological parameter and translates these values into analog signals. The signals are then digitized. Bedside monitor 102 thus records physiological information obtained from the sensor apparatus 103 and transmits the patient information to central station 101. One of ordinary skill in the art would appreciate that communication between the sensor apparatus and the monitor and between monitors and the central station may take place using any suitable wired or wireless medium and include communications based on Bluetooth, Ethernet, 802.11(x) standards, or any other wireless protocol.

Besides the measured parameter values, patient information may include any and all information contained in the patient's record, including but not limited to demographic information such as the patient's name, bed number, and the patient's identification (ID) number or the ID of the physician in charge of that patient. Optionally, the patient information can include height, weight, family medical history, X-ray information, laboratory results, and insurance information. As described in further detail below, monitors 102 typically comprise a display screen for displaying individual patient information.

In one embodiment of the present invention, the system comprises both a visual retrospective and visual prospective trending display that provides a summary of a patient's overall wellness status within a predefined time period by combining the values of a user-defined group of data elements, including but not limited to physiological parameters, weight, age, and other calculations according to a rules-based engine algorithm. For example, but not limited to such example, patient wellness may in part be calculated based upon the age of the patient and the corresponding heart rate coefficient at that particular age for a more accurate assessment. The user can thus configure the rules of the visual trending display by changing the individual parameters hard ceiling values, slope, timing, and calculations. In another embodiment of the present invention, the system comprises a visual display that provides a summary of a measured individual physiological parameter during a pre-determined time period.

Figure 2:
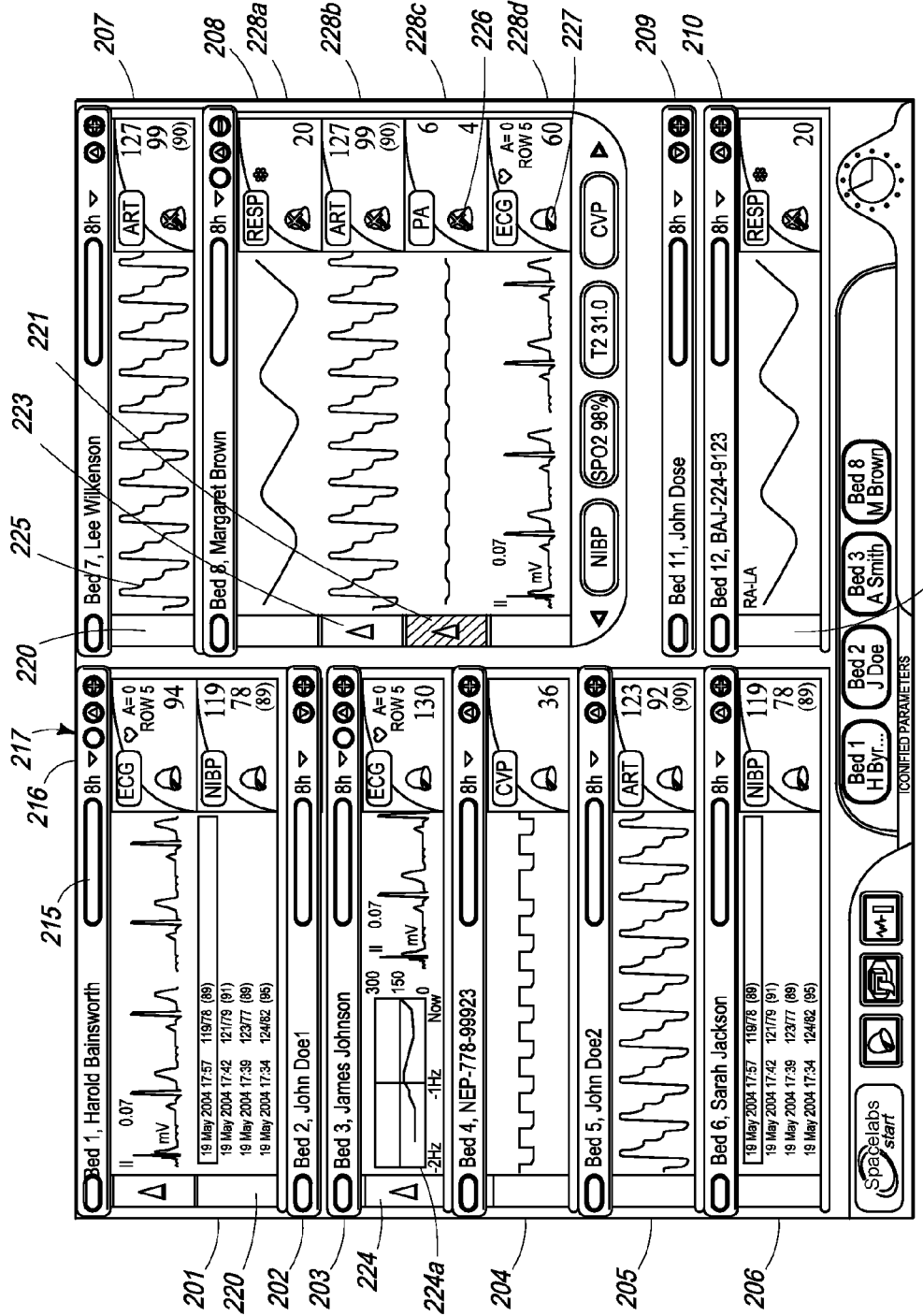
FIG. 2 is an illustration of one embodiment of a central station patient information display of the present invention.

FIG. 2 is an illustration of one embodiment of a central station patient information display of the present invention, illustrating both an overall patient wellness status trend bar and an individual parameter patient wellness status trend light bar.

In one embodiment, the central station display is divided into a plurality of sections 201, 202, 203, 204, 205, 206, 207, 208, 209, and 210 (hereinafter, referred to as sections 201-210). Sections 201-210 preferably represent individual patients and are employed to display physiological data for each patient, along with corresponding waveform, alarm and patient demographic information. In one embodiment, to allow for better patient status recognition, the spatial arrangement of individual patient sections 201-210 corresponds with the actual physical arrangement of the respective patient monitors and/or beds. For example, but not limited to such example, individual patient section 208 corresponds to the bedside monitor for the patient in Bed 8, and displays information pertaining to a plurality of physiological parameters for the patient in Bed 8, including, but not limited to ECG, $SPO_2$, and CVP.

In one embodiment, the central station display further comprises a trending display. In one embodiment, the trending display is a continuous summary of at least one measured physiological parameter of a patient. In one embodiment, the trending display is a multiple parameter overall patient wellness bar. In one embodiment, the multiple parameter overall patient wellness bar is horizontal light bar 215. In another embodiment, the trending display is an individual parameter trend bar, such as vertical light bar 220, which is described in further detail below.

In one embodiment, the trend display bars 215 and 220 employ color or the intensity of light to represent a user-defined time period. In one embodiment, the user-defined time period is displayed proximate to trend bar 215, such as time period drop-down interval menu and indicator 216 adjacent to light bar 215. The time period may be dynamically altered or adjusted by accessing the time function in interval menu and indicator 216.

In one embodiment, a plurality of colors and/or shading variations are used to differentiate the summary information presented on the trend bar. For example, in one embodiment, the trend bar is shaded the color "green" to indicate a normal or "good" condition as indicated by a calculated composite on multiple physiological parameters. In another embodiment, the trend bar may be shaded yellow to indicate an alert condition, further indicating that the calculated composite of multiple physiological parameters has entered a borderline or warning stage and are close to exceeding a pre-defined threshold value or range of values. In another example, the trend bar may be shaded red to indicate a high alert condition, further indicating that one or more elements within the physiological parameter has exceeded a pre-defined threshold value or range of values.

Optionally, the width of a wellness bar may be divided into several viewable sections with each section representing a division of the trends during a selected time frame. Each section of the "bar" may optionally be displayed in the color representative of a calculated patient overall wellness during that portion of the selected time frame.

For example, referring back to FIG. 2, for a selected patient title bar, if a patient is monitored in an 8 hour interval, the light bar represents iterations of the 8 hour time interval as different colors, indicating a different overall patient status for each section of time in the 8 hour time interval bar. As shown in FIG. 2, wellness bar 215, configured to monitor in 8 hour intervals, illustrates a recent alert where the wellness bar section has turned from a green "good" status to a yellow "alert" status, which corresponds to the patient's overall wellness.

In one embodiment, the patient monitoring system of the present invention further comprises an inference engine. In one embodiment, the inference engine is an application that is capable of running on any system host. Preferably, the inference engine is employed to determine the status of various parameters and to enable the display of trend bars and trend waveforms. One of ordinary skill in the art would appreciate that the inference engine can be installed on any computing device and be compatible with any operating system, including Linux-based, Unix-based, Java-based or Microsoft-based operating systems. The inference engine is comprised of a plurality of rules and takes into consideration the upper and lower limits for different parameters, the baseline, slope, time and other calculations, as defined by prevailing standards or as clinician-defined.

Additionally, the rules-based engine allows the clinician to define individual parameter threshold values, including but not limited to slope, timing, duration of the display bar or icon, and the combination of composite calculated values. The user can thus assign threshold values that define the range of "normal", "alert", and "high alert", among others, depending on the measured parameter and individual patient status.

Optionally, clinicians may modify inference engine rules in accordance with individual patient conditions. For example, standard blood pressure limits are 80 millimeters diastolic and 120 millimeters systolic. For patients in an older age bracket or those with a history of high blood pressure, blood pressure limits may be set to slightly higher than the standard, such as 90 millimeters diastolic and 140 millimeters systolic, as deemed safe for an individual patient by his treating physician. Thus, the patient monitoring system of the present invention provides the physician with the ability to adapt the rules that determine the status of various body parameters to suit the specific requirements of individual patients.

In one embodiment, central station display further comprises a predictive display, which is preferably an icon, such as but not limited to icon 217. In one embodiment, icon 217 is an open/close icon for parameter display rules and trend data. In one embodiment, the predictive model display icon is positioned proximate to the trending bars and displays a color indicator of the prospective trend for future patient diagnostics based upon a configurable predictive rules engine. In one embodiment the predictive icons represent a user-defined time period and employs different colors to indicate the patient status at the pre-defined time period. Data is thus collected in user-defined time increments and is preferably hierarchical when the collected data displayed is at a maximum. More specifically, the newer collected data is displayed in preference to older data.

In one embodiment, when there is no data collected during a particular time period, the trend bar or predictive icon remains clear or not colored in. In another embodiment, the monitor displays a "blank" during a time period in which no data is collected. The display bar or icon progressively migrates through the visible display area sections as time passes.

As mentioned above, in another embodiment, the trending display is an individual parameter trend bar. In one embodiment, individual parameter trend bar is vertical color light bar 220, but is not limited to such embodiment. Optionally, individual parameter trend bar remains visible to staff positioned at the central monitoring station. Optionally, different colors are used to highlight the trend bar to indicate a change in parameter values. This enables the clinicians to view simple trending information and thus ascertain individual parameter patient wellness status at a glance.

Referring back to FIG. 2, a plurality of colors and/or shading variations are used to differentiate the information presented on the individual parameter trend bar. For example, in one embodiment, trend bar 220 is shaded the color "green" to indicate a normal or "good" condition, further indicating that the physiological parameter reading from the patient is within defined safe limits. In another embodiment, trend bar 220 is shaded yellow, indicating an alert condition, further indicating that one or more physiological parameter elements have entered a borderline or warning stage and is close to exceeding a pre-defined threshold value or range of values. In another example, trend bar 220 is shaded red and illustrates a high alert condition, further indicating that one or more elements within the physiological parameter has exceeded a pre-defined threshold value or range of values.

In addition, the trend bar may further comprise shading to represent a change in the status of the rules that are employed to define safe and alarm limits for the physiological parameter for a particular patient. More specifically, but not limited to such examples, a striped trend bar 221 is indicative that one or more rules for a particular physiological parameter in the rules-based engine is deactivated. In another example, but not limited to such example, a clear trend bar 222 (i.e. one that is not colored) indicates that trending for a particular parameter has been deactivated.

In addition, in one embodiment, a vertically positioned arrow 223 may be displayed within the individual parameter trend bar to indicate the direction of change of parameter values. For example, but not limited to such example, a drop in blood pressure is represented by a downward pointing arrow ($\downarrow$) and a rise in blood pressure is represented by an upward pointing arrow ($\uparrow$), as shown in FIG. 2.

In one embodiment, the individual parameter wellness bar is capable of providing a "hot-link" to provide further details about a particular parameter. In another embodiment, the overall patient wellness trend bar is capable of providing a "hot-link" to provide a wellness bar menu, which is described in further detail below. For example, but not limited to such example, clicking trend bar 224 results in the appearance of miniature parameter trend display 224*a*, as a graph or waveform in the parameter zone. Optionally, the trend bar may be used to act as an interrogation means for perusing the electronic patient record.

Although particular colors and shading trends are described with respect to this embodiment, it should be understood to those of ordinary skill in the art that any number of colors or variations of shading or stippling may be employed. The trend bar attributes for the various parameters with the help of light bars are user-defined, and thus can be set by the healthcare professionals who use the patient monitoring system. Such attributes include the density of trend information as well as the collection duration of data included.

In one embodiment, individual parameter trend bar 220, presents individual physiological parameter information in a plurality of visual forms. For example, but not limited to such example, trend bar 220 can represent the information contained within waveform 225. Optionally, trend bar 220 information can be presented in a variety of visual forms, including, but not limited to a numerical value.

In one embodiment, individual physiological parameter alarms are based upon pre-defined user threshold value or ranges of values. The alarm status is displayed as an icon 226 for "ALARM OFF" status or icon 227 for "ALARM ON" status. One of ordinary skill in the art should appreciate that any number of relevant physiological parameters can be configured and customized to either be displayed or hidden in the plurality of sections of the central station depending upon what physiological parameters are being monitored for a patient at the bedside and/or which of those are configured to be displayed at the central station display.

Optionally, each individual patient section is further arranged into zones, such as 228*a*, 228*b*, 228*c*, and 228*d*, corresponding to individual parameters. In addition, symbols of different colors and shapes are employed to reflect the overall status of at least one individual parameter.

Figure 3:
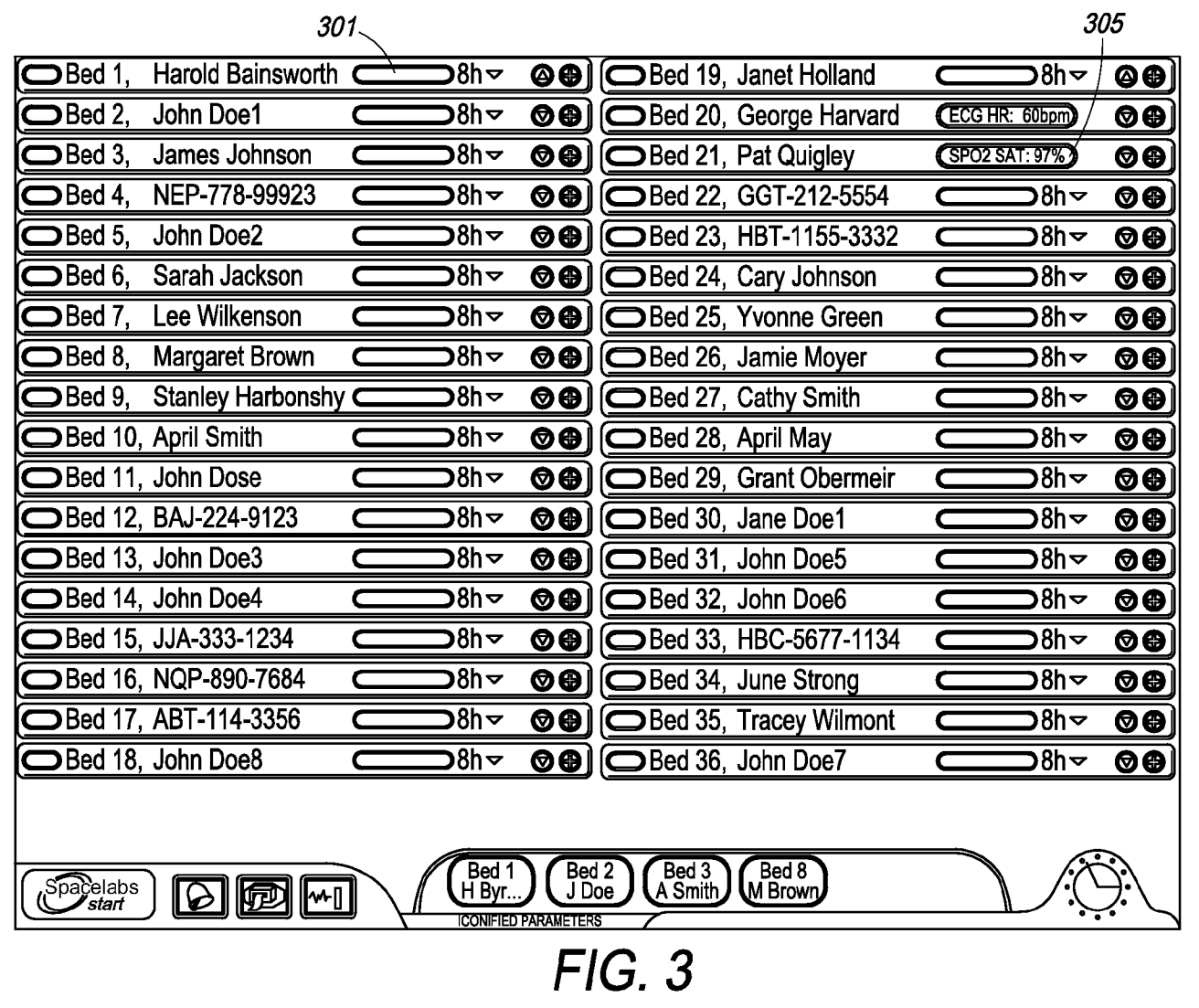

FIG. 3 is an illustration of another embodiment of a central station patient information display of the present invention. In one embodiment, central station display is capable of providing an overall patient status wellness bar 301 for at least one patient. Optionally, the trending function of the multiple parameter wellness bar can be turned off and replaced by a numerical value. As shown in FIG. 3, wellness bar 305, configured to monitor at 8 hour intervals, has been turned off and is replaced by a numerical value of at least one physiological parameter measurement. The displayed individual parameter numerical value of the central station display can be set by the clinician or can optionally scroll through a plurality of parameters at pre-defined time intervals. For example, but not limited to such example, a clinician can optionally program the system to display the heart rate of a particular patient in the cardiology unit versus overall patient wellness.

FIGS. 4A-4D are illustrations of the bedside monitor patient information display of the present invention, in which the wellness bar is activated. As described earlier the overall health state or "wellness" of a patient is a function of a plurality of user selected and defined physiological and/or demographic parameters that are interpreted and analyzed according to the configurable and user-defined rules in the rules-based engine.

In one embodiment, but not limited to such configuration the "wellness" of a patient is calculated as a function of one parameter, taking into consideration patient demographic. In another embodiment, the wellness of a patient is calculated as a function of a plurality of parameters. For example, but not limited to such example, the wellness of a patient is calculated using $SPO_2$ levels and ECG heart rate. More specifically, a calculation that incorporates the reduction in blood oxygen with a rising heart rate can be indicative of a serious problem, even though no individual parameter alarm has been triggered. The wellness parameter is thus calculated as a composite of at least one, and preferably a plurality of physiological parameters to indicate the overall health and wellness of a patient.

Figure 4A:
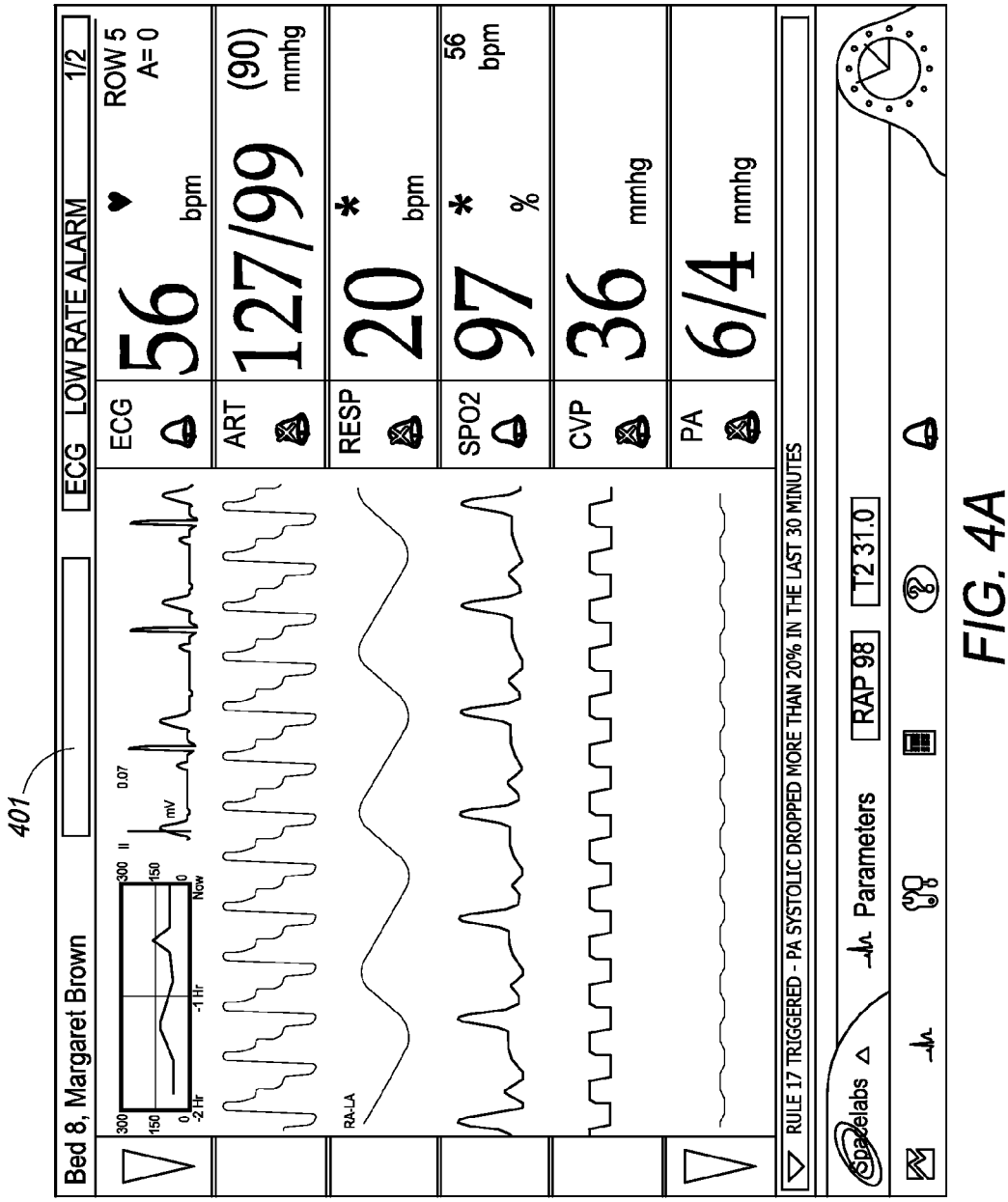
FIGS. 4A-4D depict the bedside monitor patient information display of the present invention, in which the wellness bar is established.

FIG. 4A illustrates one embodiment of a patient bedside monitor 400 of the present invention in which the wellness bar is not activated. FIGS. 4A-4D are illustrations of the operational steps of activating the wellness bar. As shown in FIG. 4A, an operator can launch the wellness bar set-up screen (not shown) by touching wellness bar area 401.

Figure 4B:
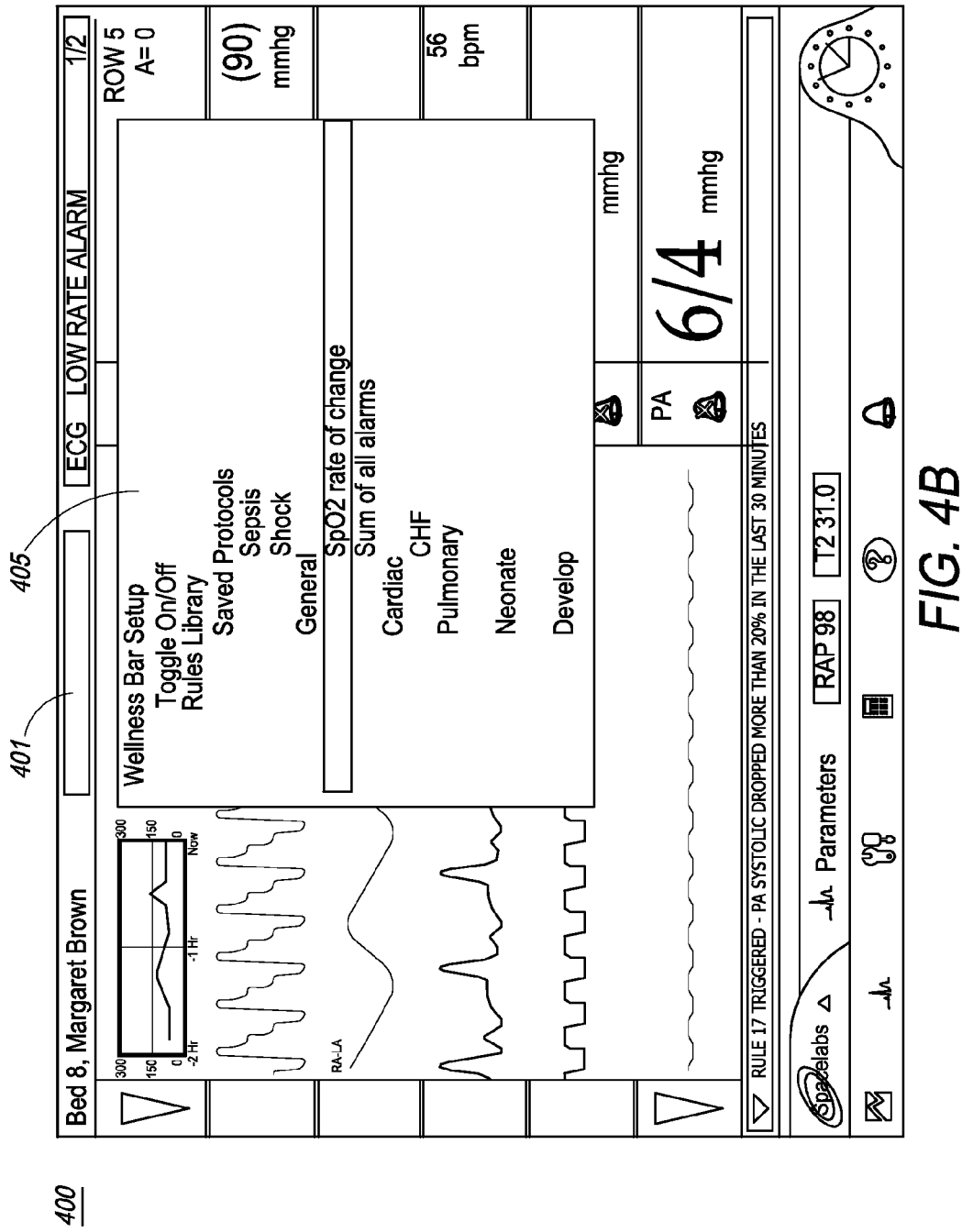
Figure 4C:
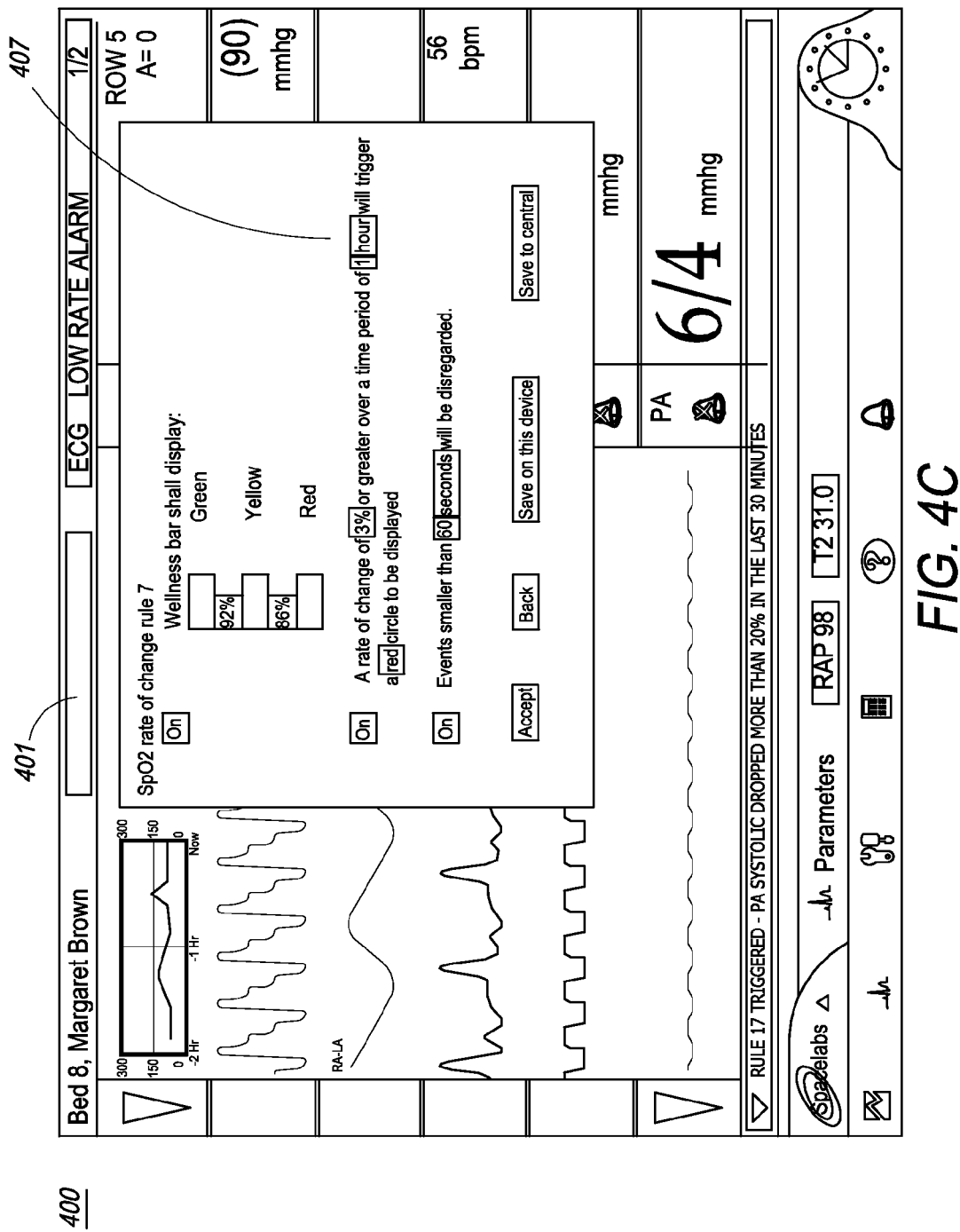

After touching wellness bar area 401, wellness bar set-up screen 405 is activated and shows the available templates and saved protocol libraries. As shown in FIG. 4B, the $SPO_2$ rate of change template is selected from wellness bar set-up screen 405. FIG. 4C depicts the $SPO_2$ rate of change template screen, which further depicts the $SPO_2$ rate of change rule. A plurality of manipulable options 407 are present on the rate of change rule screen, including but not limited to activating or deactivating the general rule, changing rule parameters, and accepting or negating the change of rule. The screen must be accepted by the caregiver in order for the changes to take effect.

Figure 4D:
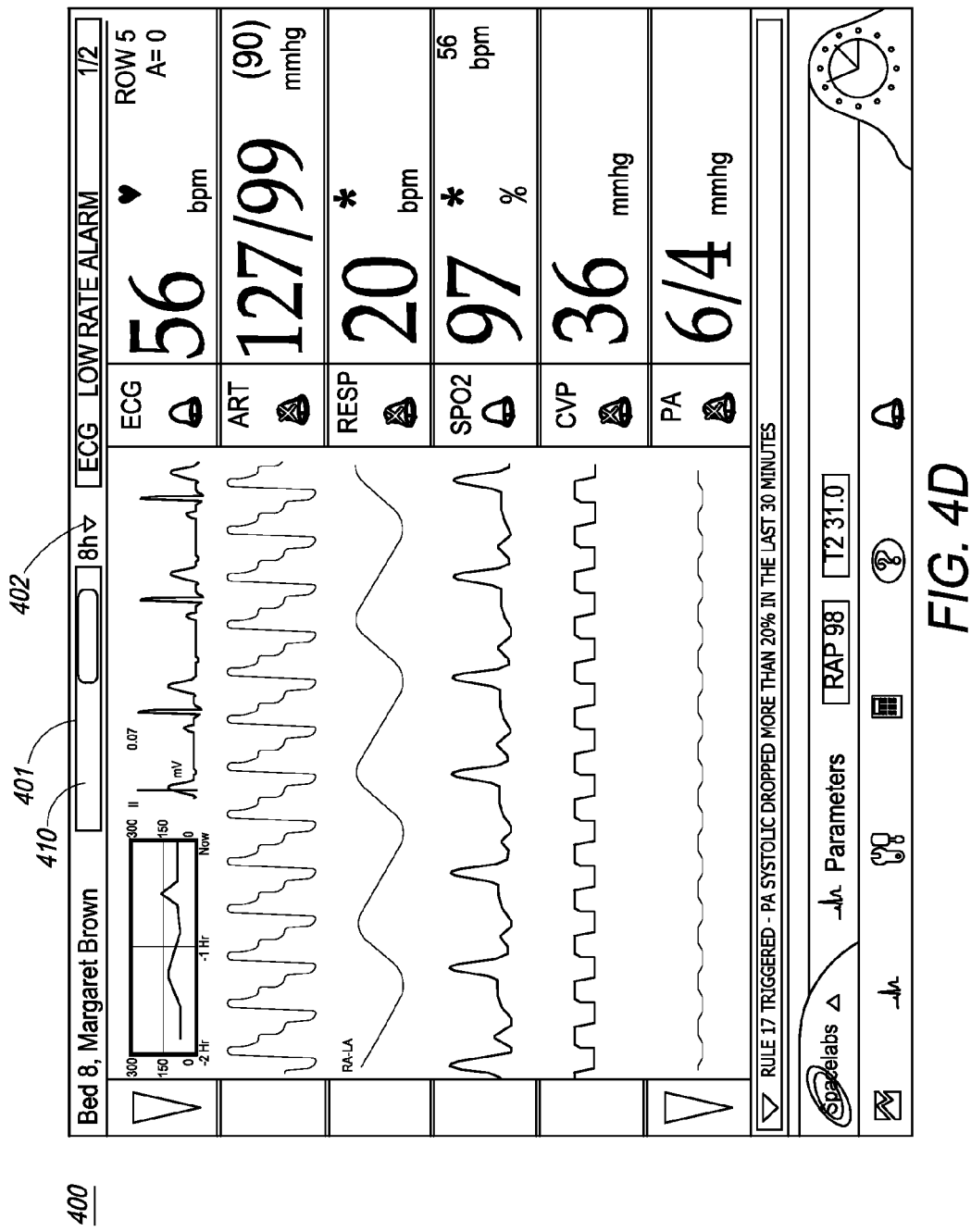

Once the changes are accepted, as shown in FIG. 4D, the wellness bar 410 is visible and active in wellness bar area 401. In one embodiment, integrated trend bar 401 is displayed as a yellow color which transitions to green which further transitions to yellow, covering the entire width of the trend bar. In one embodiment, the width of the trend bar correlates to an eight hour patient monitoring time interval, configured via time period interval drop down menu 402. Thus the patient's overall wellness is represented by the colors in the integrated trend bar, has moved from an alert state to a normal state and back to an alert state in the span of eight hours.

The wellness bar can be touched to show the rules statement, toggle the wellness indicator on or off, and give access to the trending screens. Thus, as described above, the wellness bar serves as a "hot-link" to additional data.

Referring back to FIG. 4D, wellness bar 410 is correlated with the color displayed on the central station display described with respect to FIG. 2 above, and is indicative of overall patient condition for a plurality of measured physiological parameters. In addition, as described in further detail with respect to FIG. 11 below, when light bar 1100 on top of the bedside monitor is illuminated, a clinician is able to glance into the patient room and verify the patient's status. The colors displayed, as described above, are indicative of patient status.

Figure 5:
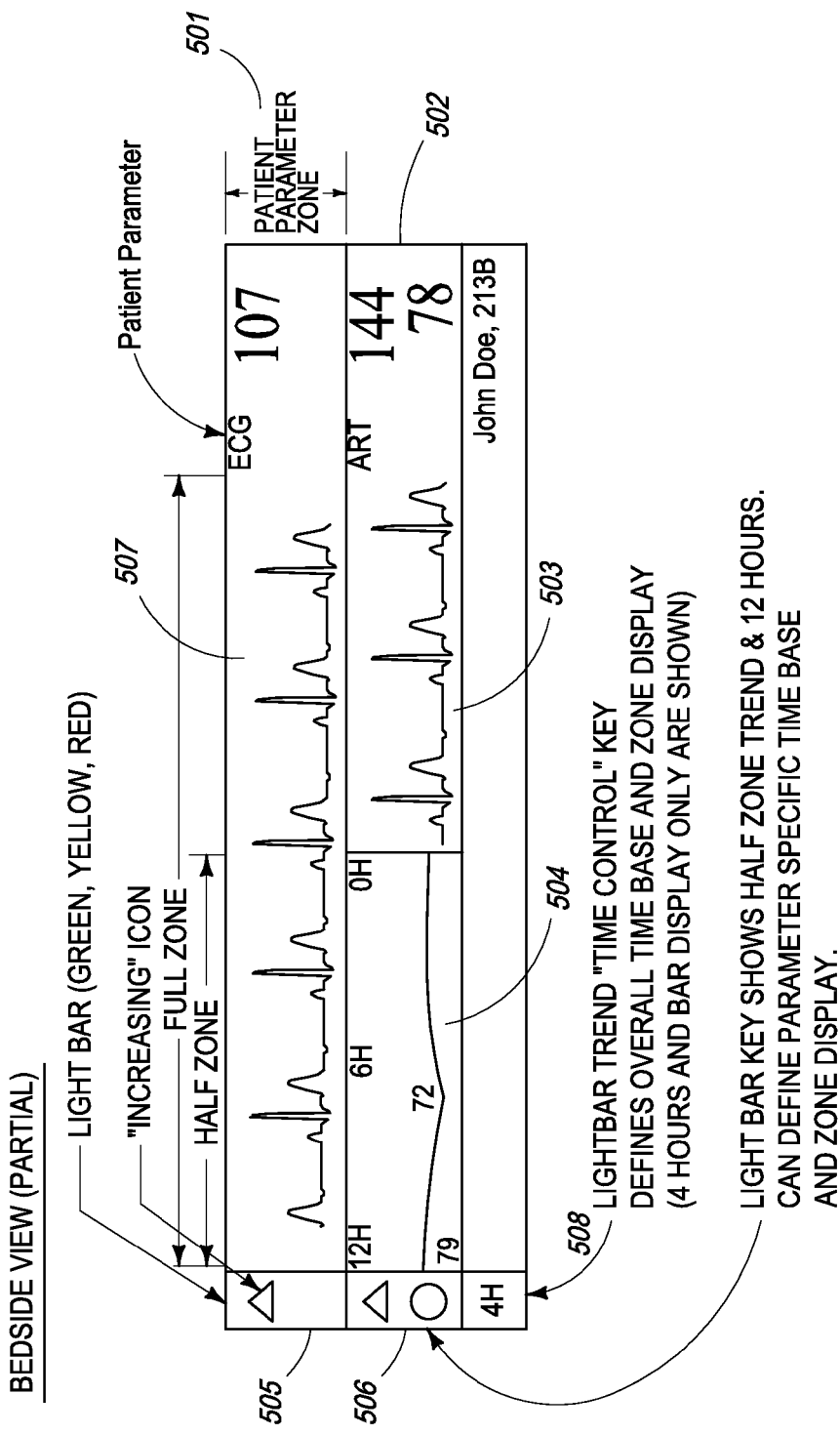
FIG. 5 depicts another embodiment of a bedside monitor patient information display of the present invention.

FIG. 5 illustrates one embodiment of a bedside monitor patient information display of the present invention, in a partial view. As described with respect to the central monitoring station display in FIG. 2, patient bedside monitor display is divided into zones, such as 501 and 502, each zone representing a specific patient parameter. In one embodiment, each parameter zone, such as zone 502, further comprises waveform area 503 reserved for displaying miniature trend graph 504 whenever required. In addition, parameter trend bars 505 and 506 are displayed adjacent to and are associated with waveform areas 507 and 503, respectively, which are employed to exhibit, at a glance, whether a particular patient parameter is within a pre-defined threshold value or range of values, as defined by the user via the rules based inference engine.

Optionally, the time display range of miniature trend graph 504 can be individually configured for each parameter. Thus, the clinician can select a time range for which she wants to view physiological parameter data. Trend bar time control key 508 is provided on the controls of the bedside monitor for selecting the time range. In one embodiment, miniature trend graph 504 displays a default time range of twelve hours.

Optionally, trend graph 504 can be configured per parameter to be in a plurality of display states, including but not limited to displayed always, displayed at the clinician's request, or automatically displayed when a trend warning occurs, as determined by the rules of the inference engine.

The trend bar may optionally be configured by the healthcare personnel to track multiple elements or attributes per parameter. For example, ECG monitoring may comprise tracking a plurality of components such as, but not limited to heart rate, arrhythmia count, and ST. The trend bar may thus be configured to individually track the elements that comprise ECG monitoring or provide a summation of the results.

Figure 6:
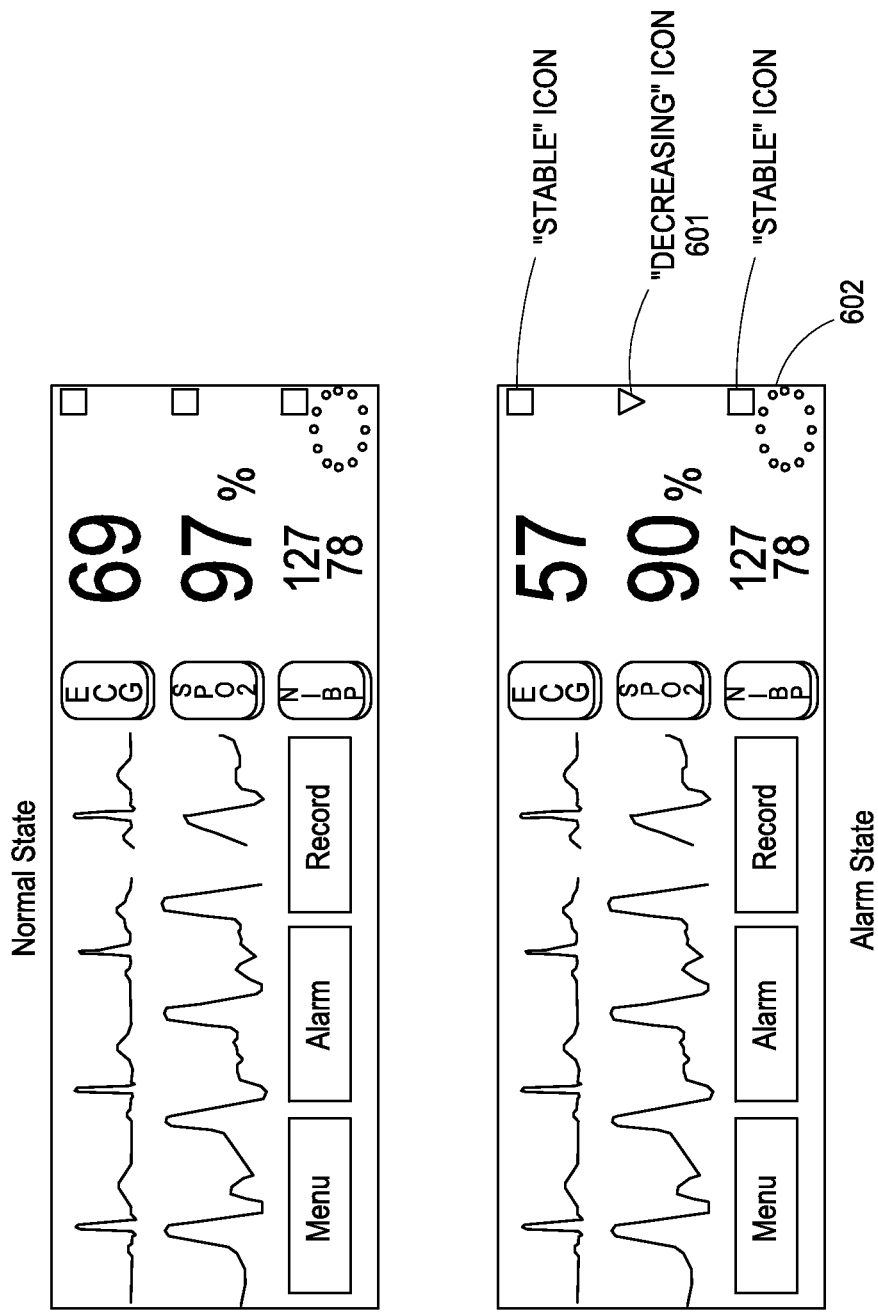
FIG. 6 is an illustration of one embodiment of a patient information display of the present invention.

FIG. 6 is an illustration of another embodiment of a patient information display of the present invention. More specifically, FIG. 6 represents a more simplified display of patient information in both a normal state and an alarm state. Different icons are used to represent the different states. As shown in FIG. 6, vertical arrow 601 is used to indicate a decrease (downward pointing arrow) in parameter value. In one embodiment, an upward vertical arrow may be used to indicate an increase in parameter value. Square block 602 is used to indicate a stable parameter status. Such visual indicators alert the healthcare provider or clinician with important information at a glance. For example, ECG data such as "20% change in ECG heart rate off baseline in last two hours, but still within the AHA approved alarm limits" can be discerned by a healthcare professional by simply looking at the display.

Figure 7:
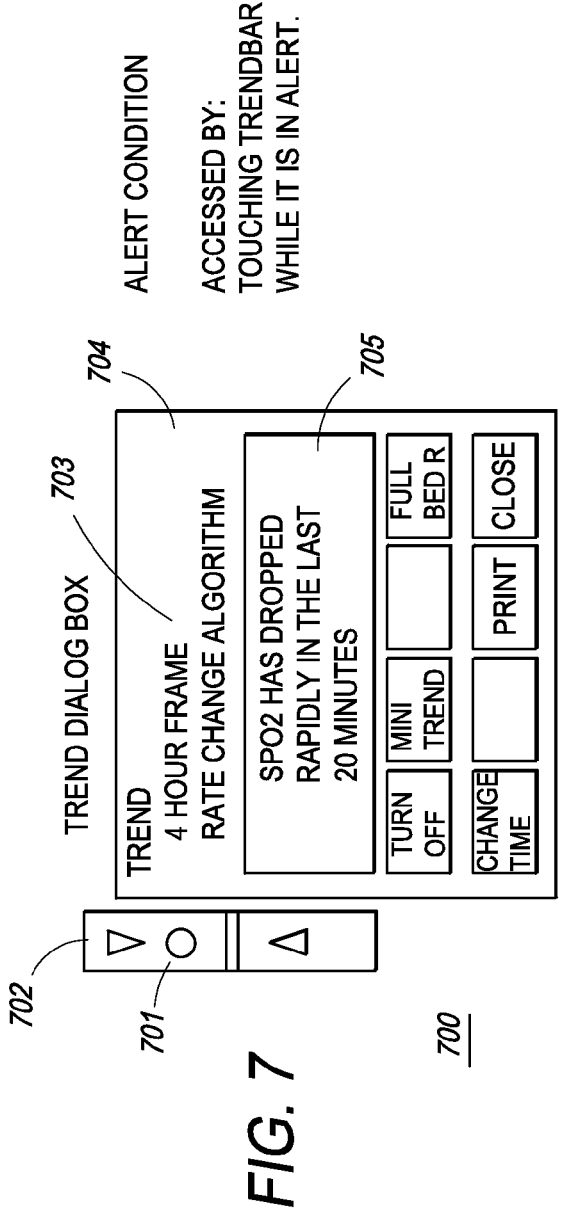
FIG. 7 depicts a trend display of the patient monitoring system of the present invention, further illustrating an alarm or alert condition.

FIG. 7 depicts a trend display of the patient monitoring system of the present invention, further illustrating an alarm or alert condition. In one embodiment, the nature of the alert condition is accessed by touching trend bar 701 while it is in an alert state. In one embodiment, the alert state is displayed by a trend alert arrow 702. In one embodiment, trend alert arrow 702 is pointing downwards to indicate a decrease in patient wellness. Display 700 is well-defined for ease of use by the clinician. In addition, display 700 provides information on the status of the alert condition, including but not limited to the time interval 703 and the parameter change 704, and a summary of information 705, such as but not limited to "SPO$_2$ has dropped rapidly in the last 20 minutes". In addition, other relevant information is displayed, such as the algorithm employed to determine the change in SPO$_2$ and its resultant alert condition.

Figure 8:
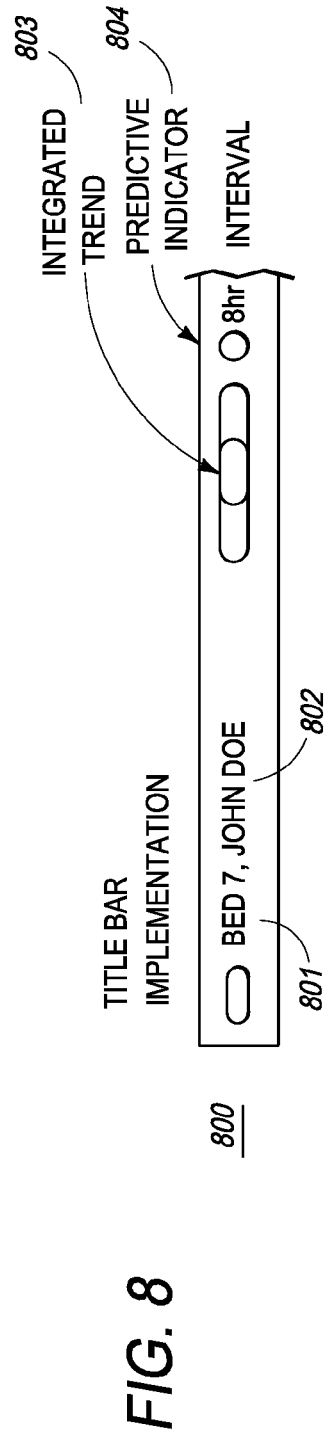
FIG. 8 depicts an integrated trend display of the patient monitoring system of the present invention, further illustrating a patient status title bar.

FIG. 8 depicts an integrated trend display of the patient monitoring system of the present invention, further illustrating a patient status title bar as shown at the central station. Patient status title bar 800 is also described with respect to FIGS. 2 and 3 above. The central station view comprises at least one, and preferably a plurality of patient status title bars 800.

Patients are listed by bed number 801, name 802, and overall patient status. The overall patient status is indicated by integrated trend bar 803 that combines each measured patient parameter into an overall status indication and predictive model icon 804 that indicates overall patient status, as described above. In one embodiment, predictive model icon 804 is a predictive indicator dot.

Figure 9:
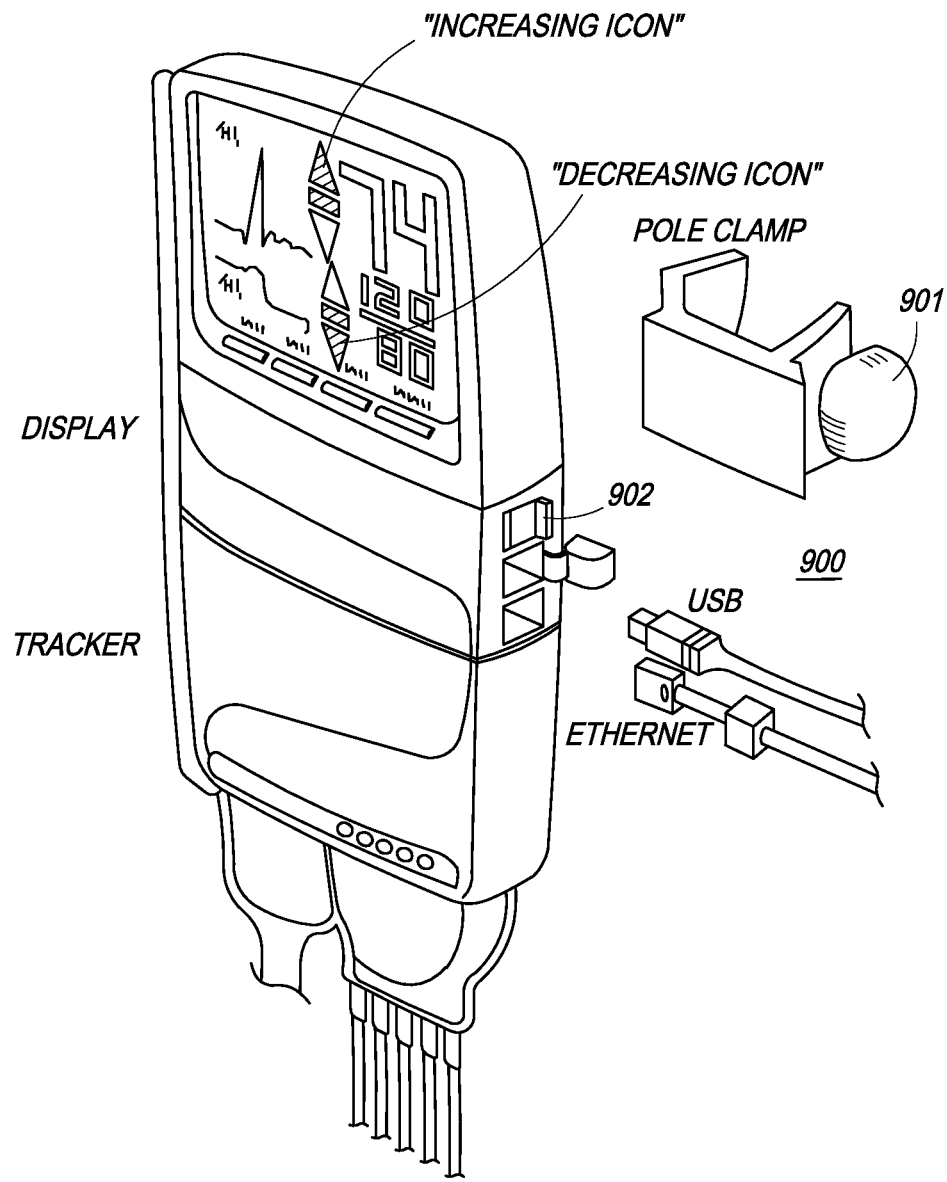
FIG. 9 depicts one embodiment of a bedside monitor patient information display of the present invention.

FIG. 9 depicts another embodiment of a bedside monitor patient information display of the present invention. More specifically, as shown in FIG. 9, in one embodiment, the patient bedside monitor may be handheld, portable unit 900. Optionally, handheld, portable monitor unit 900 may be a fixed unit when using pole clamp 901. Portable monitor unit 900 further comprises peripheral interface 902, allowing it to be linked to an external computing device such as a PC or a laptop. Data regarding a patient's condition may be transmitted to the computing device and stored for further processing, analysis and/or retrieval. The configuration of peripheral interface 902 may vary, depending upon the type of connection to the external computing device. For example, data may be transmitted from the bedside monitor to a PC over a wired link. Thus, peripheral interface 902 may comprise a USB port or RS232 serial connection for communication with the PC.

Additionally, bedside monitor 900 may optionally be equipped with the ability to transmit data by means of a wireless link, such as by radio waves or infrared. Thus, peripheral interface 902 may comprise a transmitter (not shown) capable of transmitting radio waves or an infrared signal to a computing device, which is configured to receive radio waves or an infrared signal. As shown in FIG. 9, bedside monitor 900 may optionally be placed in communication with other bedside monitors by including an Ethernet capability in peripheral interface 902. In this manner, all the bedside monitors, along with the central station may be interconnected into a high-speed local area network (LAN).

In addition to its use in the hospital and intensive care environments as described above, the patient monitoring system of the present invention may also be used to provide feedback to individuals engaged in exercise or physical activity. Such feedback is particularly useful for athletes and sportspersons, as it helps them in accurately measuring their progress. Two major parameters used for determining general health and physical fitness and monitoring optimal training levels are heart rate (in beats per minute) and the level of oxygen in blood. The physiological monitoring system of the present invention includes sensors for measuring heart rate and an oximeter for measuring blood oxygen level. Further, as described above with respect to FIG. 9, portable patient monitor unit 900 is suitable for use to provide real-time continuous feedback on the physiological parameters during the period of physical activity. For example, the display unit may be configured to be worn around a human user's waist, or may be configured to be mounted to a bicycle (e.g., mounted to the handlebars). The monitoring system may also be configured to display data on a treadmill display screen so that the monitoring system will provide heart rate and blood oxygen data for a subject walking or running on a treadmill. Irrespective of the location, the system has the ability to provide critical data and their analyses to the user at a single glance. The monitoring system also includes audible or visual alarms, which are activated when data for a physiological parameter does not meet a predetermined target. Thus, when a user's blood oxygen level or heart rate exceeds or falls short of a predetermined target, the user is instantly alerted. This is especially useful when a person is trying to achieve a particular fitness or training level.

Figure 10:
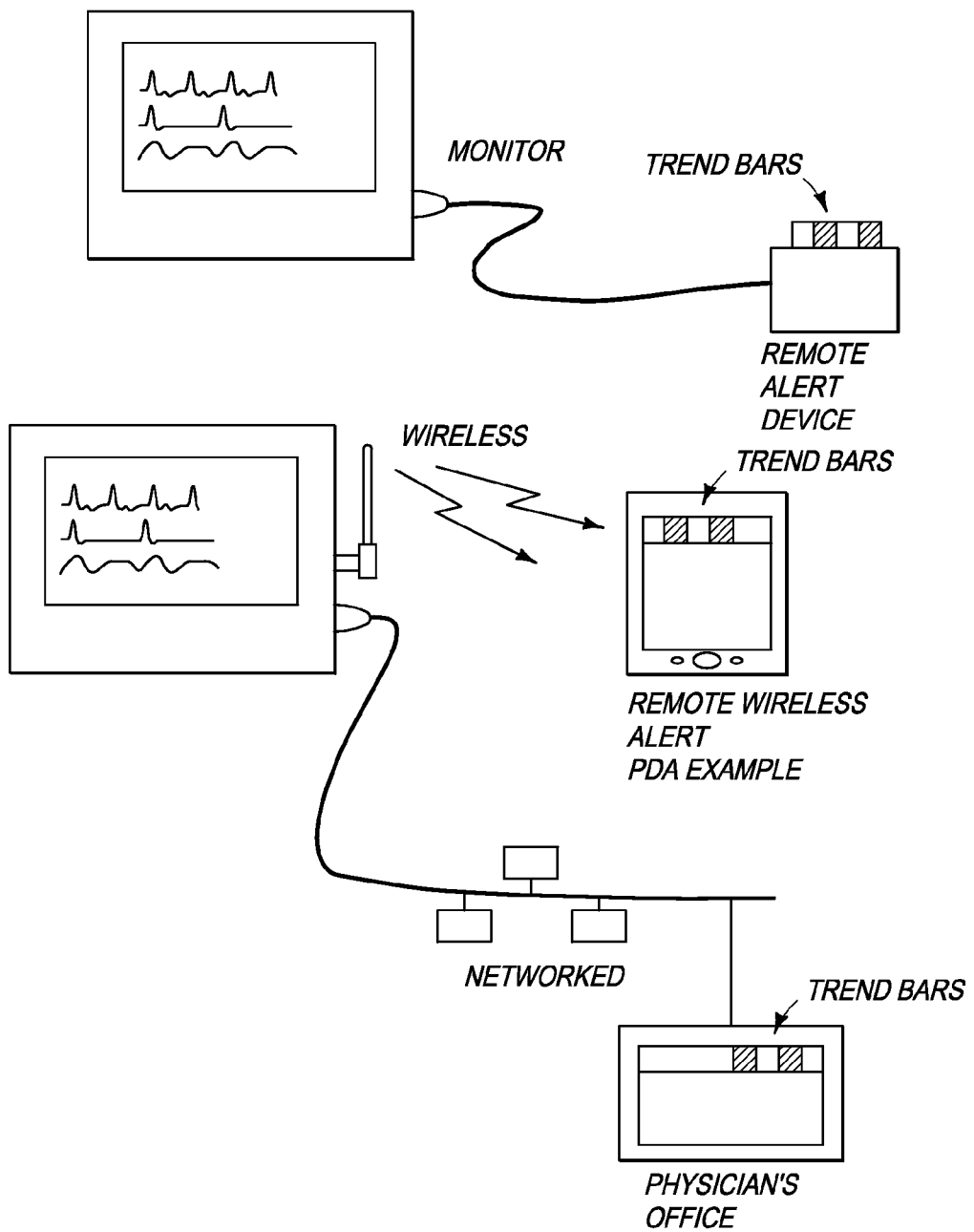
FIG. 10 is a diagram illustrating the interconnectivity and operation of the patient monitoring system with continuous trending display of the present invention, as employed in a clinical setting.

FIG. 10 is a diagram illustrating the interconnectivity and operation of a patient monitoring system with continuous trending display of the present invention, as employed in a clinical setting. Thus, the continuous multi-parameter summary trending display wellness bar and predictive model "icon" are displayed via intensity or colors on a central display, a bedside monitor in the patient room, wireless devices, networked devices, and remote displays, depending on the needs and requirements of the clinical setting. Thus, patient status is always accessible by the clinician at a glance. For example, in one embodiment, referring back to FIG. 9, the multi-parameter summary bedside display is a portable, hand-held unit. The details of such unit have already been described with respect to FIG. 9 and will thus not be repeated herein.

Figure 11:
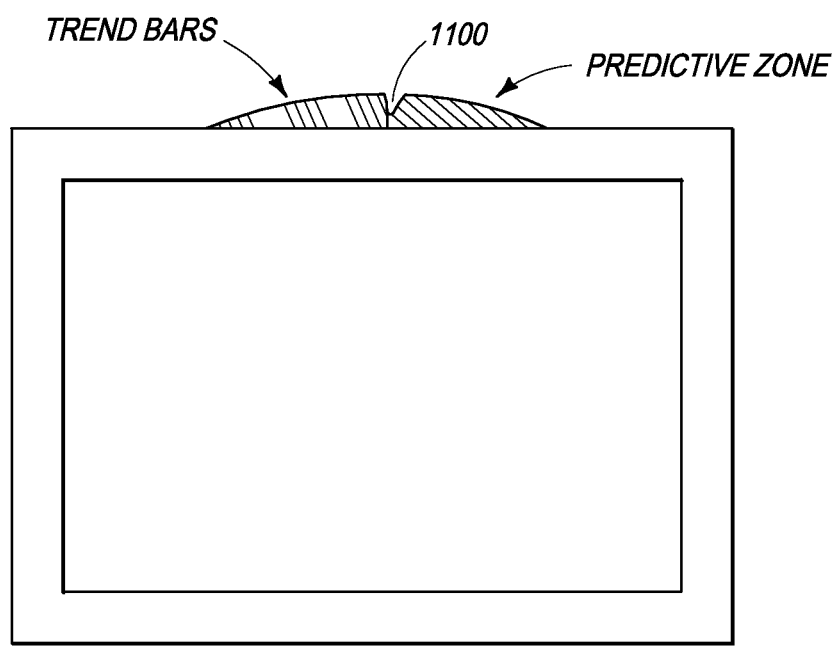
FIG. 11 is an illustration of a patient wellness trend bar as implemented on a nurse alert light.

FIG. 11 is an illustration of a patient wellness trend bar implemented as a clinician alert light, as described above. Referring back to FIG. 1, in one embodiment, monitor 102 further comprises a translucent bar that serves as a "nurse alert". Translucent bar 1100 comprises a series of LEDs (not shown) of different colors, such as but not limited to red, green and yellow. In one embodiment, the translucent bar is capable of displaying at least one or a plurality of colors to indicate the trending that is on the wellness bar. Thus, the translucent bar serves as a rough indicator of the wellness bar status of the patient, allowing a nurse or other clinician to easily glance into a patient room and access patient wellness status with respect to a combination of a plurality of physiological parameters. In particular, the translucent alert bar can be used in those situations where display areas are limited in scope, pixel size, and capability.

In another embodiment, the present invention is directed towards methods of and apparatuses for searching for, manipulating, customizing and displaying information related to monitored physiological parameters. It should be noted that the embodiments herein are described, by way of example only, with reference to a patient bedside or central monitoring station as described above. The embodiments described herein, however, may be used with any display that communicates with any monitoring system.

In one embodiment, the graphical user interfaces of the present invention are generated on a processor in data communication with a memory. In one embodiment, the memory stores physiological parameter data obtained from at least one or a plurality of sensors. Further, the processor executes a plurality of instructions to generate an interactive user interface based upon physiological parameter data obtained from the sensors.

Thus, one of ordinary skill in the art would appreciate that the interfaces of the present invention are created using a processor executing instructions. Further, one of ordinary skill in the art would appreciate that the interface features described in the present application are enabled by source code, compiled into an executable application and executing on a processor. The processor can be any type of computing device, including a laptop, personal computer, personal digital assistant, cell phone, server, or specialized medical device. Additionally, the programmatic code can be compiled into a single application, executing on a single processor, or distributed among several different processors operating locally or remotely to each other.

Figure 12:
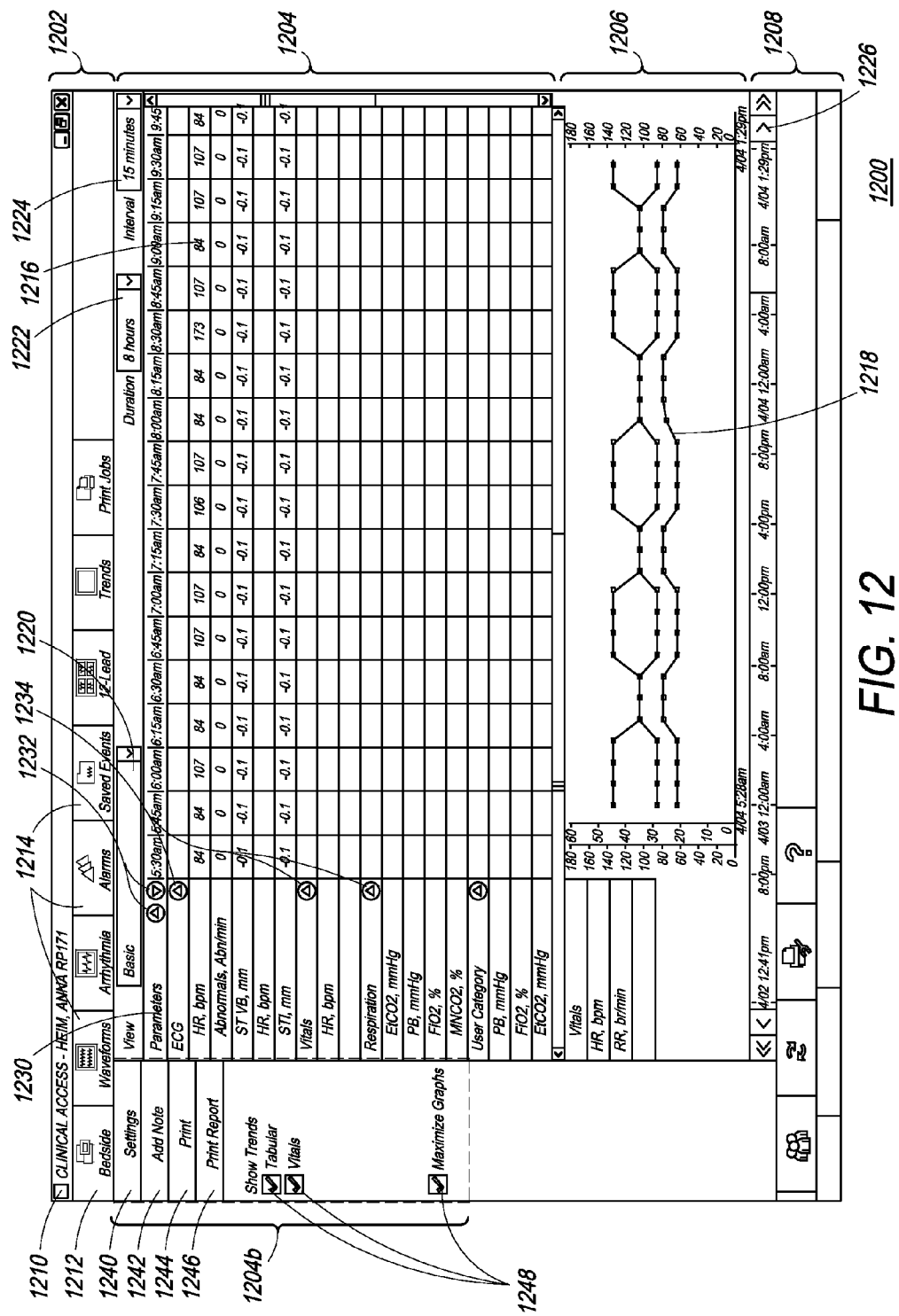
FIG. 12 is an illustration of one embodiment of an interactive graphical user interface in which a plurality of monitored patient parameters are presented in a time-based, easy-to-format table and/or waveform.

FIG. 12 is an illustration of one embodiment of an interactive graphical user interface 1200 in which a plurality of monitored patient parameters are presented in a time-based, easy-to-format table and/or waveform. In one embodiment, interactive graphical user interface 1200 comprises first region 1202, second region 1204, third region 1206, and fourth region 1208. In one embodiment, first region 1202 comprises a top portion of the interactive graphical user interface. In another embodiment, second region 1204 comprises an upper middle portion of the interactive graphical user interface 1200. In one embodiment, third region 1206 comprises a lower middle portion of the interactive graphical user interface. In one embodiment, fourth region 1208 comprises a bottom portion of the interactive graphical user interface.

In one embodiment, first region 1202 comprises a patient name area 1210 and a menu bar area 1212. In one embodiment, menu bar area 1212 further comprises at least one menu icon or button 1214. In one embodiment, the at least one menu icon or button 1214 comprises buttons that can be used to access previously recorded data, such as "waveform" button, "trends" button, and "alarms" button. In one embodiment, at least one menu icon or button 1214 comprises dedicated buttons for monitoring parameters that reflect specific heart conditions, such as, but not limited to an "arrhythmia" button for viewing arrhythmia status and a "12-lead" button for 12-lead ECG reports. Optionally, if the present invention is used at a central monitoring station, the bedside button is employed to view the parameters being monitored and displayed at the patient's bedside. In one embodiment, the at least one menu icon or button 1214 includes, but is not limited to a "bedside" button, a "waveforms" button, an "arrhythmia" button, an "alarms" button, a "saved events" button, a "12-lead" button, a "trends" button, and a "print jobs" button.

In one embodiment, second region 1204 comprises at least one view of measured values of physiological parameters presented in accordance with a time of measurement. In one embodiment, the at least one view is a table 1216.

In one embodiment, third region 1206 comprises at least one view of measured values of physiological parameters presented in accordance with a time of measurement. In another embodiment, the at least one view is a graph or waveform 1218 representative of at least one measured physiological parameter presented in the table in second region 1204. In one embodiment, different views of patient parameters can be accessed by selecting the "trends" menu button 1214, as will be discussed in greater detail below.

In one embodiment, fourth region 1208 comprises time slider 1226 for allowing a user to search the time database to view data recorded at any given time and at specific intervals.

In one embodiment, drop-down view selection menu 1220 is provided in second region 1204 of the interactive graphical user interface for selecting the presentation view of the table in second region 1204. In one embodiment, available views include, but are not limited to adult, pediatric, and neonatal. In one embodiment, drop-down selection view menu includes a custom view option that allows the user to customize and name a view for display selection.

In one embodiment, drop-down duration selection menu 1222 is also provided in second region 1204 of the interactive graphical user interface for selecting the time duration presented in each table, in increments of hours. In one embodiment, drop-down interval selection menu 1224 is also provided in second region 1204 of the interactive graphical user interface for selecting the time interval between each reading, which, in the present example, is set at 15-minute intervals.

In one embodiment, once the "trends" menu button 1214 is selected, as shown in FIG. 12, the default view is table 1216 in second region 1204. In another embodiment, at least one waveform 1218, representative of at least one measured physiological parameter presented in table 1216, is displayed in third region 1206. In one embodiment, table 1216 presents the history and trends of various parameters 1230 including but not limited to ECG, Vitals, Respiration and optional user selected categories recorded and thus, based on a time interval measurement, is displayed in an easy-to-read tabular format. Optionally, the parameter table may include up/down arrows 1232 for scrolling between at least one and preferably a plurality of parameters.

Still optionally, the parameter table may include individual menu expansion arrow 1234 for toggling between a compressed and expanded individual parameter menus.

Figure 14:
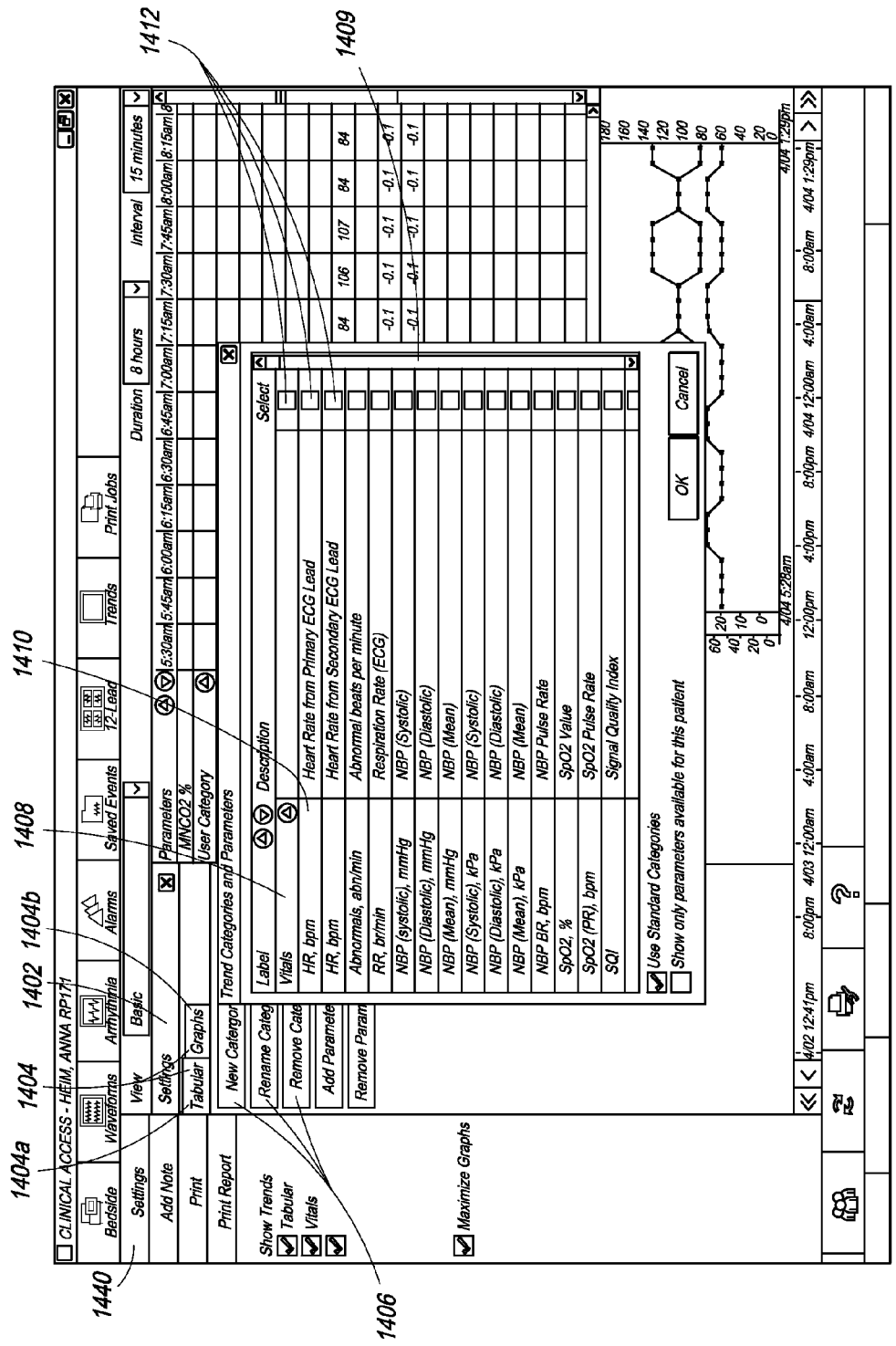
FIG. 14 is an illustration of one embodiment of a graphical user interface which presents a list of parameters that can be user-customized for display in a table.

Optionally, second region 1204 of interactive graphical interface screen 1200 may further include sub-region 1204b, on the left side of the interactive graphical user interface 1200, for providing "settings" button 1240, "add note" button 1242, "print" button 1244, and "print report" button 1246. "Settings" button 1240 is described in further detail with respect to FIG. 14. "Add note" button 1242 is used to allow a clinician to add notes to a particular table, graph or event representation. "Print" button 1244 is used to print the current view of the interface. "Print Report" button 1246 is used to print a customized report of patient parameters and patient views, according to clinician guidelines. Still optionally, sub-region 1204b may further include checkboxes 1248 for "Show Trends". In one embodiment, available checkboxes 1248 are "tabular" and vitals". When selected "tabular" and "vitals" provide a tabular view of measured vital patient parameters.

Figure 13:
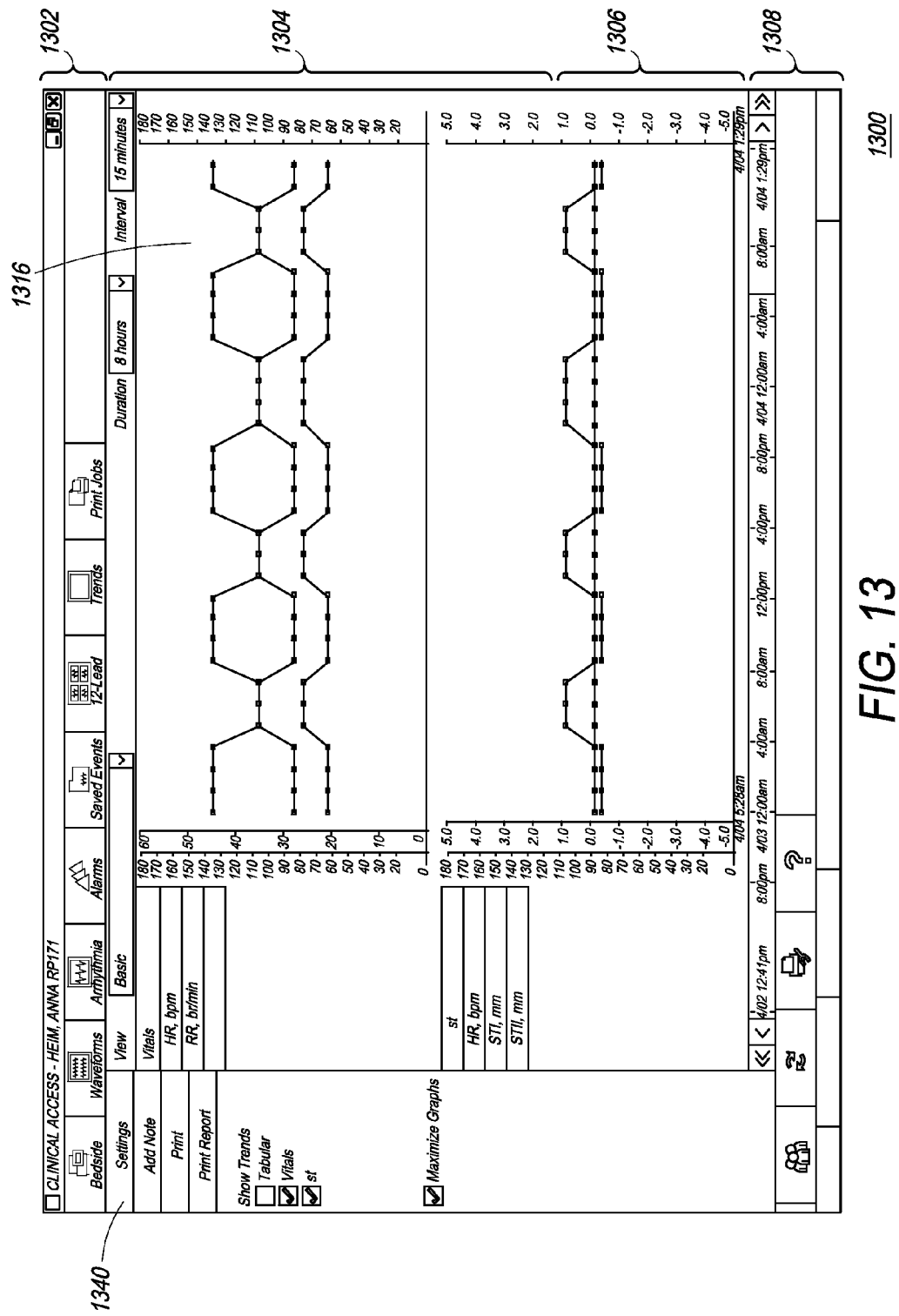
FIG. 13 is an illustration of one embodiment of an interactive graphical user interface in which a graph displaying recorded parameters is presented.

In another embodiment, when the tabular button is not selected, the default view is a graphical representation, as shown in FIG. 13; thus, second region 1304 displays a waveform graph instead of a table. Thus, in one embodiment, a waveform is displayed in both regions 1304 and 1306.

Now referring to FIG. 13, an illustration of one embodiment of a graphical user interface 1300 in which at least one graph displaying recorded parameters is presented. As mentioned above, with respect to corresponding numerals in FIG. 12, graphical user interface 1300 comprises first region 1302, second region 1304, third region 1306, and fourth region 1308. First region 1302 has been described in detail with respect to FIG. 12 above and will not be described herein.

In one embodiment, multiple parameters are illustrated in at least one graph 1316, presented in second region 1304 of interface 1300. For example, graph 1316 depicts two parameters, namely, HR and RR, recorded over a time frame of 8 hours. These parameter graphs provide a quick view of patient status thereby assisting in the decision making process.

As shown in FIGS. 12 and 13, the interface screen of the present invention further provides a "settings" button, indicated as 1240 and 1340, respectively, for selecting display settings. Now referring to FIG. 14, an illustration of one embodiment of a graphical user interface 1400 is shown, which presents a list of settings that can be selected and user-customized for a specific care area. Now referring to FIG. 14, "display settings" window 1402 is shown. Display settings window 1402 opens upon selecting settings button 1440, also shown in FIGS. 12 (1240) and 13 (1340), and provides at least one tab 1404 that can be selected to customize the display of the corresponding parameter data in tabular or graph format. In one embodiment, tab 1404a, when selected, provides a list of categories that can be manipulated with respect to "tabular" display settings while tab 1404b, when selected, provides a list of categories that can be manipulated with respect to "graph" display settings (described in further detail with respect to FIG. 15).

In one embodiment, selecting tab 1404a provides the user with a list of manipulable categories 1406, such as but not limited to "new category", "rename category", "remove category", "add parameter", and "remove parameter". In one embodiment, upon selection of "add parameter" tab 1406, scrolling menu 1408 appears, comprising a parameter list 1410 and checkboxes 1412 next to the name of each parameter. If a checkbox 1412 is selected, the corresponding parameter 1410 is included in the table.

A user can select parameters from the table 1410 using scroll-down menu 1408. Still further, the user can use up/down controls 1409 to arrange the parameters in a particular order for display in the table. A "remove parameter" button is provided on the screen that can be used to remove a parameter from table display.

Figure 15:
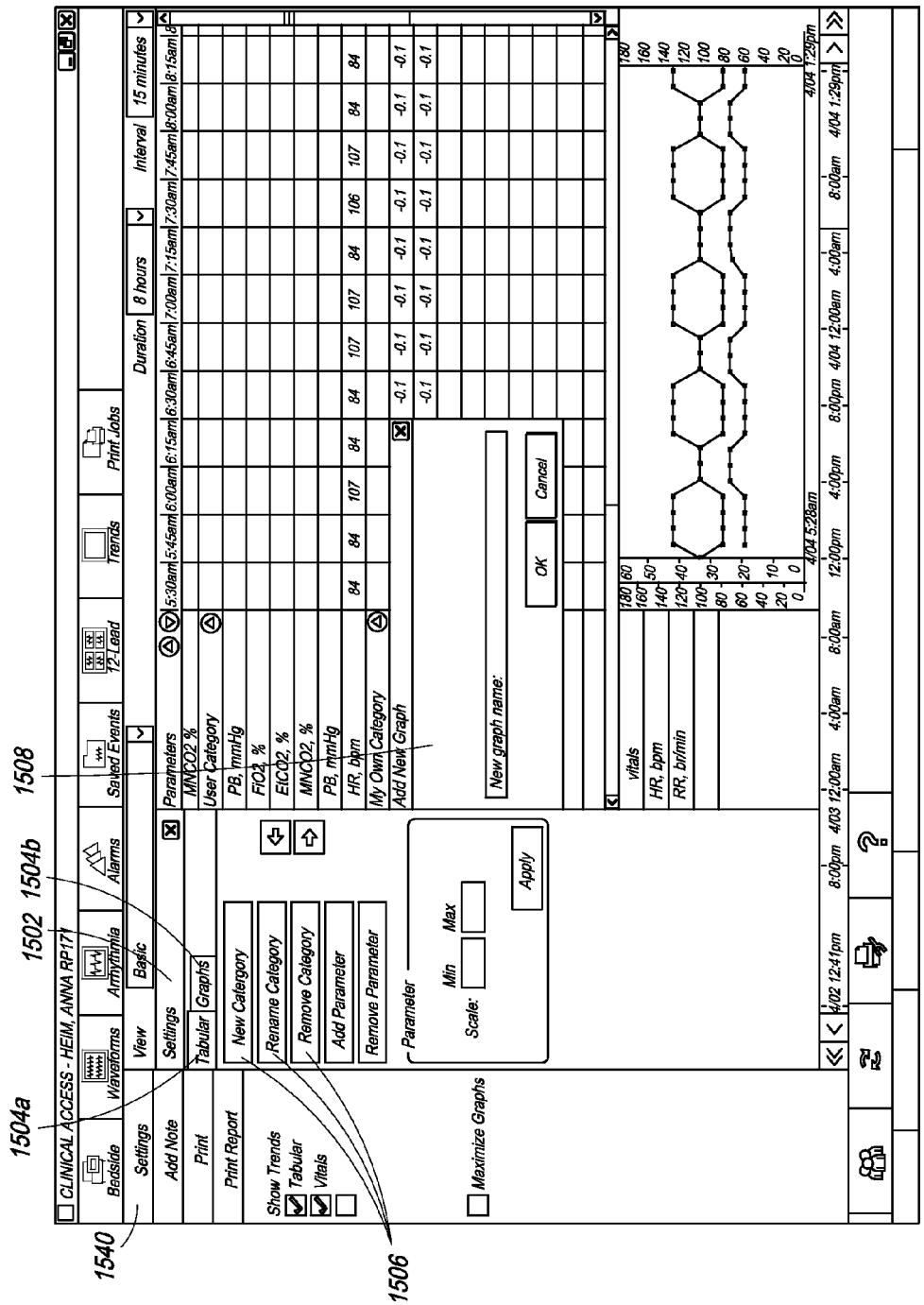
FIG. 15 is an illustration of one embodiment of a graphical user interface which presents a list of parameters that can be user-customized for display in a waveform.

FIG. 15 is an illustration of one embodiment of a graphical user interface 1500 which presents a display 1502 of graph settings and parameters that can be user-customized for a specific care area, upon selecting "settings" button 1540. As described with respect to FIG. 14, tab 1404b, referred to as tab 1504b in FIG. 15, provides a list of categories that can be manipulated with respect to "graph" display settings. In one embodiment, selecting tab 1504b provides the user with a list of categories 1506, such as but not limited to "new graph", "rename graph", "remove graph", "add parameters", and "remove parameters". In one embodiment, upon selection of "new graph" tab 1506, a pop-up window 1508 appears, prompting for a new graph name. It should be noted herein that each tab functions similarly. Thus, for example, upon selection of "remove graph", a pop-up window appears, prompting for the required action effectuating the change in display, such as confirming the removal of the graph.

In another embodiment, the present invention is directed towards an interactive graphical user interface and software-based search tool for the rapid analysis of multi-parameter data. In traditional hospital settings, physicians are required to write daily progress notes summarizing the health status of patients under their care. In one embodiment, the search tool of the present invention helps to provide a rapid objective summary of coexisting physiological events.

In another embodiment, the search tool of the present invention generates a visual representation of physiological parameters as the search output. In one embodiment, the visual representation of physiological parameters includes a summary of collective physiological parameters as defined in the search criteria. In addition to a high level summary of events, the visual representation is also equipped with the ability to navigate through the lower level details of physiological data. Thus, in one embodiment, the multi-parameter search tool of the present invention works retrospectively and allows clinicians to see when multiple physiological parameters values are greater than, less than, or equal to individual critical thresholds per parameter for a specific duration.

In one embodiment, the search tool allows the physician to review retrospective parameter data and a summary of events to decide upon an appropriate treatment regimen that is patient-specific. In another embodiment, the search tools allows for facile identification of unstable clinical events, such as, but not limited to a sudden decrease in heart rate.

In one embodiment, the search tool of the present invention is employed to identify situations in which a patient has recurring abnormal changes in vital signs, such as, but not limited to respiration, heart rhythm, or blood pressure which may be caused by problems in patient's vital organs such as the heart, lungs, neuromuscular system, or central nervous system. The search tool of the present invention is advantageous is that it quickly provides a summary of specific pathological and/or physiological events and the number of times that those events occurred, thereby providing a fast analysis of data and enabling quick response on the part of the physician.

In addition to providing information on vital physiological parameters, in one embodiment, the search tool of the present invention incorporates data obtained from medical devices, such as but not limited to, life support equipment (ventilators and the like), dialysis equipment, and infusion pumps. In another embodiment, the search tool of the present invention also incorporates data obtained from laboratory tests such as, but not limited to, hemodynamic techniques.

In one embodiment, the user (physician) can customize the search tool to obtain data relevant to a single parameter for a combination of criteria for different parameters. For example, but not limited to such example, a search query may be entered that requires the Heart Rate to be less than 50 beats per minute (bpm) for more than 15 seconds, and the Blood Pressure to be less than 80 mmHg Systolic for more than 15 seconds. The search results that are presented for this query are those which satisfy both criteria. Once a user identifies search criteria, the search query as well as the search results can be saved such that if required again, it can be selected and activated in negligible time.

Figure 16:
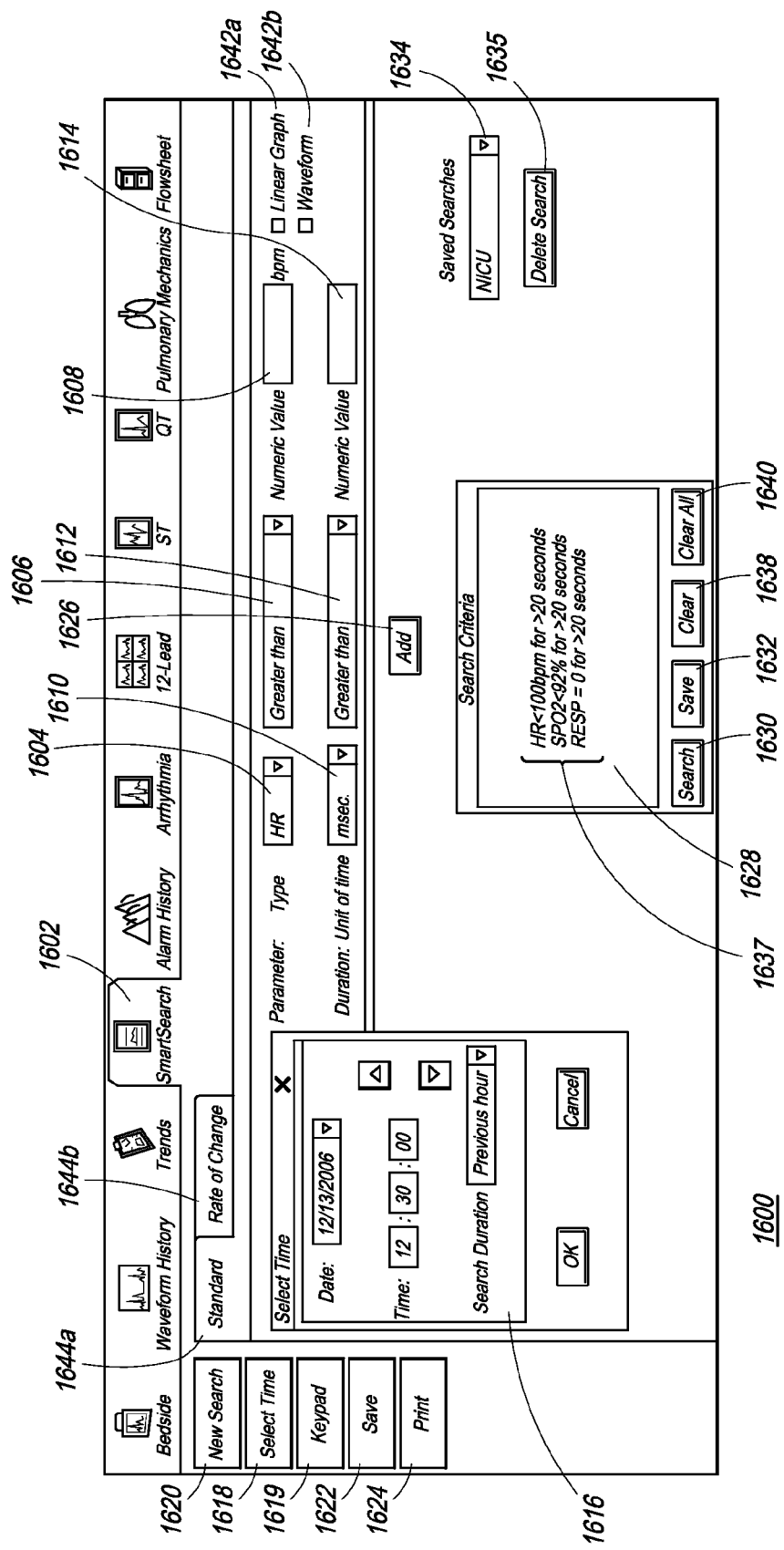
FIG. 16 is an illustration of one embodiment of a search tool application, shown on an interactive graphical user interface (GUI) screen.
Figure 17:
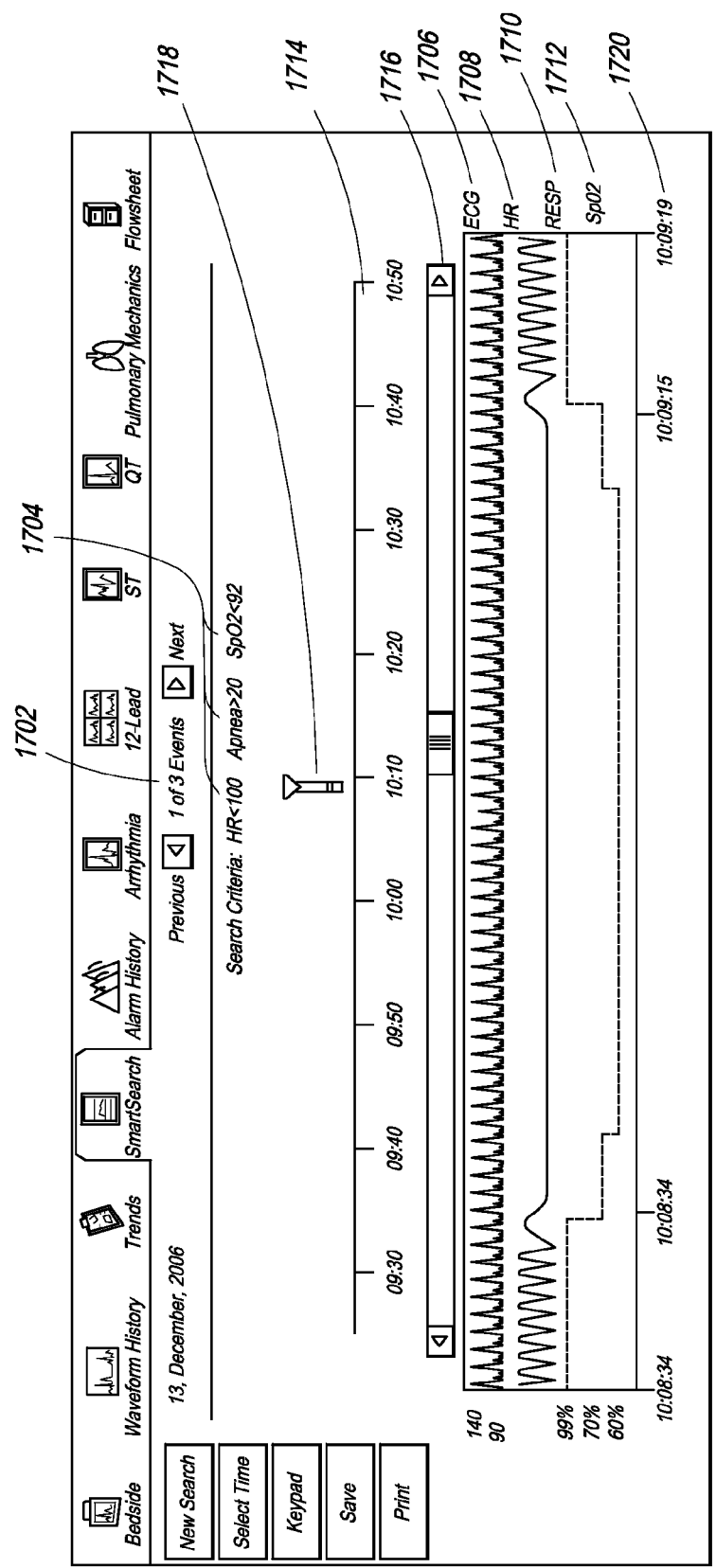
FIG. 17 is another illustration of one embodiment of a search tool application, shown on an interactive graphical user interface (GUI) screen.

Referring back to FIG. 12, the at least one menu icon or button 1210 includes a "SmartSearch" button. Upon selecting the SmartSearch button, a user is directed to a graphical user interface that comprises a search tool application. FIGS. 16 and 17 are illustrations of one embodiment of an exemplary search tool application, shown on an interactive graphical user interface (GUI) screen.

Referring now to FIG. 16, an interactive graphical user interface (GUI) screen 1600 is shown, for example and not limited to such example, as monitoring the vital signs of a neonatal patient with premature respiratory system. In one embodiment, and as described with respect to FIG. 12, the interface screen 1200 is equipped with "SmartSearch" button 1210 for enabling the search tool of the present invention. In this example, owing to the premature respiratory system, the neonatal patient may simultaneously stop breathing and experience a rapid decline in both heart rate (HR) and oxygen saturation (which is traditionally measured peripherally via pulse oximetry ($SpO_2$)). These three vital sign changes may be entered as search criteria to detect events.

Search criteria may be entered on the interface screen by selecting the parameter type from a drop-down list 1604, selecting "Greater than", "Less than" or "Equal to" from a list 1606 for comparison to a numerical value, and entering the numerical value in the box 1608. Similarly, the duration criteria for a given event, such as a decline in heart rate, may be entered by selecting the unit of time such as milliseconds (msec), seconds, minutes etc, from a list 1610, selecting "Greater than", "Less than" or "Equal to" from a list 1612 for comparison to a numerical value, and entering the numerical value in the box 1614.

Date, time and duration (such as the previous hour) search constraints for searching the specified physiological parameters can be selected using the 'Select Time' menu 1616 provided on the interactive interface screen 1600. The 'Select Time' menu 1616 is available when the 'Select Time' button 1618 is activated from the set of buttons on the left side of the interface screen. Other buttons in this set include, but are not limited to, those for initiating a new search 1620, for saving the search result data 1622 and for printing the search results 1624. Optionally, to facilitate data entry for search queries, the interface 1600 provides a touch-screen keypad, which can be activated using "Keypad" button 1619.

After specifying each search criterion, when a user clicks on the 'Add' button 1626, the specified criterion is displayed in the search window 1628. Thus, in one embodiment, the 'Add' button serves to confirm the search parameters that are specified and added to the search by the user at each addition.

In one embodiment, multiple search criteria may be specified, as shown in search window 1628. For example, but not limited to such example, a search query may be entered as follows:

HR<100 bpm for >20 seconds, AND
SpO$_2$<92% for >20 seconds, AND
Respiration RESP=0 for >20 seconds.

By clicking on search button 1630, the user initiates the search and search results are subsequently displayed.

Optionally, search criteria can be saved using "save" button 1632. In one embodiment, searches are saved by a user-selected title. For example, the present search query is saved under the name 'NICU', and can later be accessed using "saved search" scroll-down menu 1634. Saved searches may be deleted using 'delete' button 1635.

Still optionally, individual search criteria may be cleared from search window 1628 by highlighting the individual search criterion 1637 and subsequently activating 'clear' button 1638, and all search criteria may be cleared using 'clear all' button 1640.

Still optionally, a user may specify whether the user wants the search results to be displayed as linear graph or as waveform, by selecting the appropriate check box 1642*a* or 1642*b*, respectively. A user can also select the parameter graphs to be displayed in the standard format or as rate of change over a defined time period using the tabs 1644*a* and 1644*b*, respectively. The "Rate of Change" (of one or more parameters) option allows the user to search for events defined by a parameter change by a given number of units over a specified duration, within a specified period of time.

The 'Rate of Change' option is particularly advantageous in cases where during the course of a treatment given to a patient, the physician wants to know if, for example, less than X units of change occurred in a certain parameter over N duration, at a specified time. This may help the physician decide, for example, if vasoactive or intotropic drugs need to be titrated. In another example, a 'Rate of Change' search may be employed to monitor the rate of change in elevation and depression of cardiac parameters, for assessment of myocardial ischemic changes.

When physiological parameters of patients are being monitored, physicians prefer to have the recorded parameter data in the form of graphs and tables. When presented in this manner, it helps the physicians to quickly and efficiently assess large amounts parameter data for evaluating the patient status and reviewing the treatment plan being followed. However, the responsibility of preparing graphs and tables is usually given to nurses or paramedics who are often unaccustomed with dealing with data in this manner. Further the possibility of human error in manual charting of data also tends to be more. Therefore, in one embodiment, the system of present invention provides a quick and simple technique to format tables and graphs for optimal viewing. The dependence of inter-related patient parameters is quickly visualized in the graph format of the present invention, which facilitates decision making.

FIG. 17 is an illustration of another embodiment of a search tool application, shown on a graphical user interface (GUI) screen 1700, and more specifically, showing the various physiological events corresponding to the search query described with reference to FIG. 16. Referring now to FIG. 17, scroll menu 1702 is provided to indicate the number of events that occurred according to the specified search criteria 1704 and to allow a user to scroll between these events. In one embodiment, all parameters that fit the specified criteria for a particular event are shown for the specified event duration.

In one embodiment, the parameter waveforms for the events are displayed on the same graph. Accordingly, the waveforms for ECG 1706, HR 1708, Respiration (RESP) 1710 and SpO$_2$ 1712 are displayed on the screen.

In one embodiment, a timeline is provided on the interface screen so that the waveform display is time-referenced. A section of an exemplary timeline 1714 is illustrated in FIG. 17, showing the duration between 9:30 and 10:50. In one embodiment, the timeline is based on the date, time, and duration selection described above with reference to FIG. 16. In one embodiment, a slider 1716 is used to select a viewing portion of the timeline. A pointer 1718 on the timeline indicates the duration of time corresponding to displayed waveform graphs or events. For example, as shown in FIG. 17, slider 1716 is positioned such that the duration between 10:08:34 and 10:09:19 is visible, illustrated by 1720, which corresponds to an event, that is also indicated by pointer 1718.

With a specific query-based summary display, the physician or user is able to ascertain the status of parameters of interest without looking at several hours of recorded data and charts. Generally, physicians spend countless hours reading through charts to determine whether the parameters of interest have remained unchanged, improved, or become more frequent or longer in duration, compared to the patient's progress notes from the day before.

In hospital environments, practitioners do not always see or hear every alarm occurrence for each patient. Therefore, in another embodiment, the present invention also includes an "Alarm History Bar" for providing a visual presentation of the most recent alarms. In one embodiment, the alarm history bar is displayed on a real-time graphical user interface located on a central station or a bedside monitor. By presenting recent alarm history data on the first level of the real-time interface, a clinician can immediately ascertain which alarm events occurred in their absence. Also, the alarm history bars are designed such that a clinician may navigate to more comprehensive data such as parameter waveforms and linear trends from an alarm history bar, thereby providing the necessary data to judge the clinical severity of the patient.

The alarm history bar of the present invention advantageously provides rapid access to the details of the most recent alarm events including the numeric value which triggered an alarm, the parameter threshold setting, and the priority of the alarm. These details are contained in a database of alarm events. From the alarm history bar, a clinician can select a particular event or events and automatically navigate to the alarm history database to review the comprehensive details of the selected alarm event(s).

Figure 18:
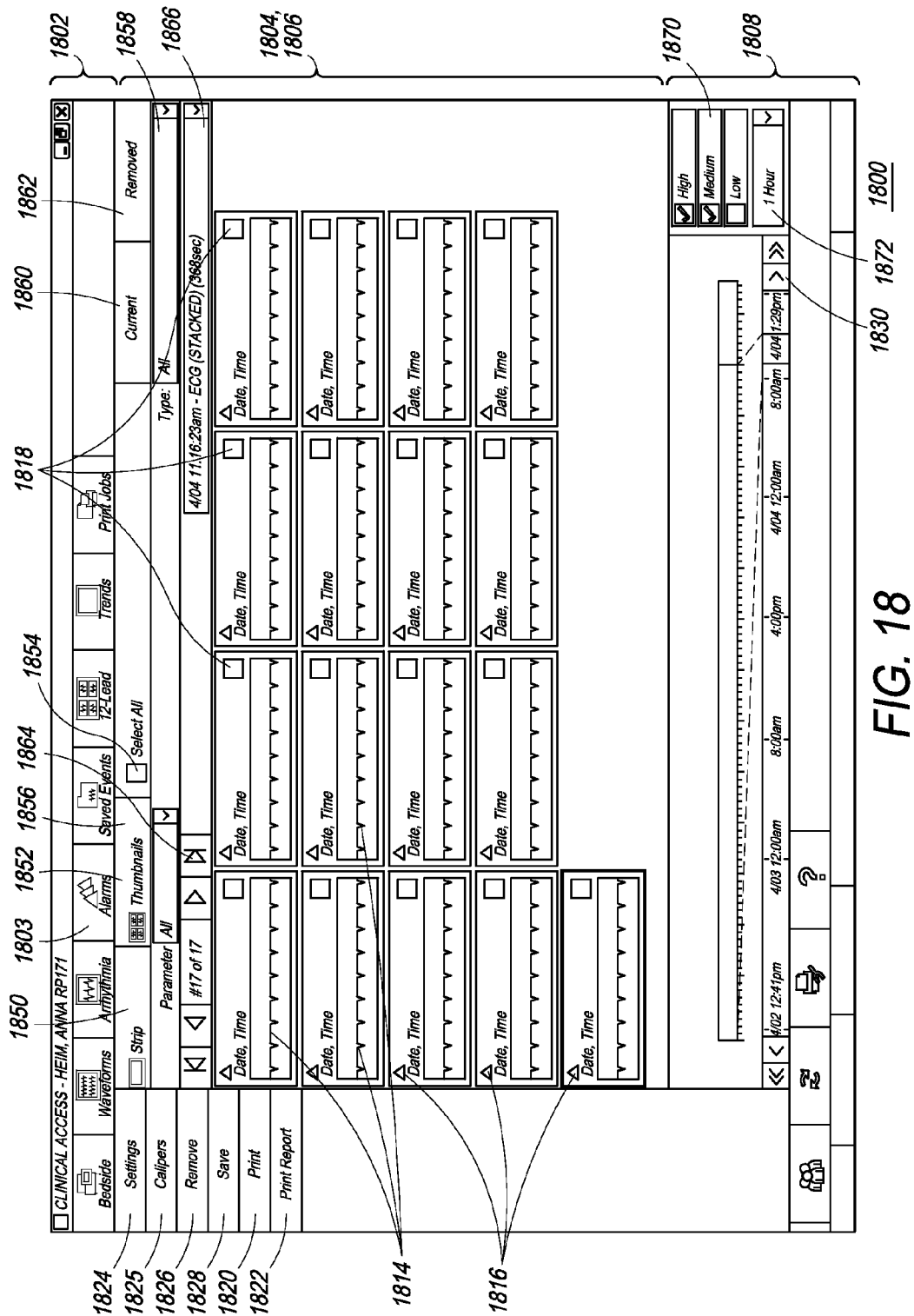
FIG. 18 is an illustration of one embodiment of a graphical user interface, showing graphical trends and details of selected alarm events.

FIG. 18 is an illustration of one embodiment of a graphical user interface 1800, showing graphical trends and details of selected alarm events. First region 1802 has already been described with respect to FIGS. 12 and 13 above and will not be described herein. As shown in FIG. 18, the details of various alarm events are displayed in second region 1804 and third region 1806 of interface screen 1800 when the 'Alarms' tab 1803 is selected. Alarm details for various parameters are displayed in at least one window 1814, and include graphical trends, date and time and priority for the alarm. In one embodiment, the priority for each alarm event is indicated by a coded triangle 1816 in the corresponding alarm window. It should be understood by those of ordinary skill in the art that a coding scheme can be of any type, including color-coding, stippling, shading, and the like. A checkbox 1818 is also provided in each alarm window 1814, which can be used to select particular alarm events. The selected alarm events can be printed using "print" button 1820 and a report can be printed using "print report" button 1822. In addition, interface 1800 may optionally include an "alarm settings" button 1824 for editing alarm settings, a "calipers" button 1825, a 'remove alarm' button 1826 for removing selected alarms from display, and a "save" button 1828 for storing alarm events. Calipers button 1825 is included to provide the user with at least one, and preferably a plurality of electronic calipers that can be used to make measurements directly on the waveform. In one embodiment, available calipers include, but are not limited to "rate", "QRS", "QT", "PR", and "Amplitude". It should be noted that multiple calipers can be used on the same waveform to measure necessary parameters.

Still further, second region 1804 and third region 1806 of graphical user interface 1800 provides at least one of, but not limited to, the following options to the user for customizing the display:

'Strip' 1850, which allows the users to view alarm events in a long, horizontal strip format.

"Thumbnail" 1852, which allows the users to view alarm events in thumbnail format, as shown in FIG. 18.

'Select All' 1854 for allowing the user to easily select all alarm events.

Parameter Selection Drop-Down Menu 1856 for selecting at least one parameter for which to display alarms.

Type Selection Drop-Down Menu 1858 for selecting a type of alarm event.

Current Selection Button 1860 for selecting and displaying current alarm events.

Removed Selection Button 1862 for selecting and displaying removed alarm events (historical).

Left-Right Scroll Menu 1864 for scrolling between a plurality of alarm events.

Individual Alarm Event Drop-Down Menu 1866 for selecting individual alarm events for display.

Further, fourth region 1808 of interface 1800 includes a time slider 1830 for selecting a date and time interval for which the clinician wants to view alarm events. Further, fourth region 1808 of interface 1800 includes a checkbox selection menu 1870 for choosing to display, low, medium, and/or high priority alarm events. Still further, fourth region 1808 includes a drop-down menu 1872 for selecting the time interval of displayed alarm events.

An additional important aspect of physiologic monitoring is reviewing a patient's significant clinical events and alarms. The traditional approach for displaying events and alarms is to utilize some type of histogram. In such presentations a histogram bar represents the sum of all events that occurred within the time interval specified by the histogram resolution. A major drawback of this approach is that the events are commingled together and that the start, end, and duration of individual events are not represented. In other words, individual events may be masked or hidden by overlapping events occurring over the same time period. Further, the information in a histogram presentation is highly processed and requires a firm grasp of technical concepts such as histogram resolution. Moreover a histogram provides a very generalized interpretation of events in that something happened around a certain time; however determining what exactly happened and when requires further analysis of recorded data.

Figure 19:
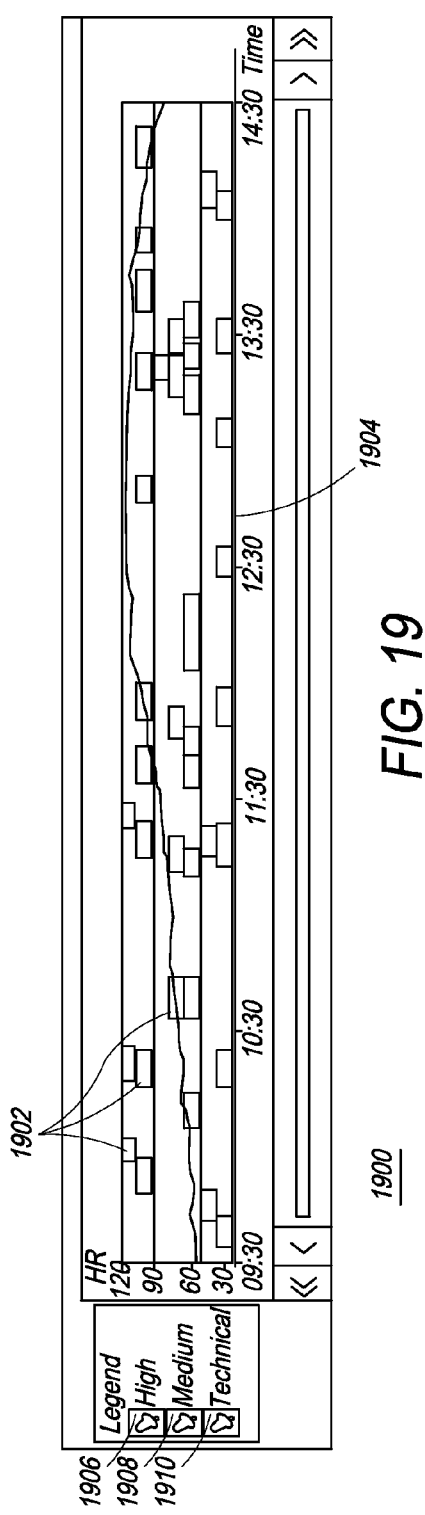
FIG. 19 is an illustration of one embodiment of a graphical user interface presenting an expanded view of banded graphs.

In order to address these problems, one embodiment of the present invention employs a novel concept, known as a "banded graph", to represent all clinical events, even if some or all of them occur within the same period of time. For this purpose, the present invention makes use of an algorithm to automatically space overlapping events into different bands, thus ensuring that not a single clinical event is lost or obscured by other events, potentially occurring at the same time. An exemplary interface screen illustrating banded graphs is shown in FIG. 19. In this example, multiple alarms for one parameter (HR) are displayed as different bands 1902 along a timeline 1904, even if they have occurred at the same or overlapping periods of time. Optionally, the events sorted by their priority. Optionally, the events are coded to designate priority. In one embodiment, different colors are used to represent different priorities. Thus, in one example, as can be seen from FIG. 19, events (alarms) are classified into 'High' 1906, 'Medium' 1908 and 'Technical' 1910 priority levels. In one embodiment, the different priority level alarm events are associated with a different color representing each event, such as red, yellow and blue for high, medium, and technical, respectively. Further, in one embodiment, the bands for high priority events are positioned at the top of the screen so that they are easier for the user to see at a glance. One of ordinary skill in the art would appreciate that events may be categorized on the basis of any criteria and that the present invention is not limited to a priority categorization. Furthermore, the algorithm used in the present invention also preserves the duration of each event relative to a time scale, that is, the width of each band indicates the duration of the event it represents. This further helps in identification of the events that have the highest clinical significance.

Thus, the use of banded graphs in the system of the present invention are advantageous (among other advantages) because they a) fully represent the information contained in single events; b) preserve the start time, stop (ending) time, and the duration of each event; and c) represent each event along a shared time line while retaining all information. Further, each event in a banded graph can be addressed individually and thus provide a direct link to descriptive information constituting the event/alarm. Still further, events are clustered together by certain criteria such as, but not limited to, priority and can be made to stand out using additional visual cues.

Figure 20:
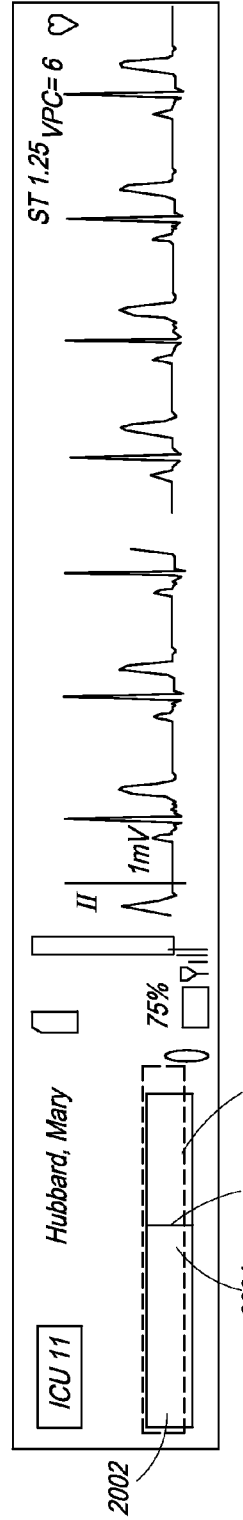
FIG. 20 is an illustration of one embodiment of a graphical user interface presenting an alarm history bar.

FIG. 20 is an illustration of one embodiment of a graphical user interface presenting an alarm history bar 2002, which is displayed upon selection of an "alarm history" button, described with respect to FIGS. 12 and 18. The frequency of alarm events is displayed on bar 2002, in one embodiment. In another embodiment, bar 2002 is representative of a known period of time. As shown in FIG. 20, three alarm events 2004, 2006 and 2008 are displayed. In one embodiment, the width of the displayed events 2004, 2006 and 2008 correlates to the duration for which the corresponding parameter was in alarm. Thus, a wider event display represents a longer alarm event.

Optionally, the events are labeled, such as by color coding, to represent different parameters.

Figure 21:
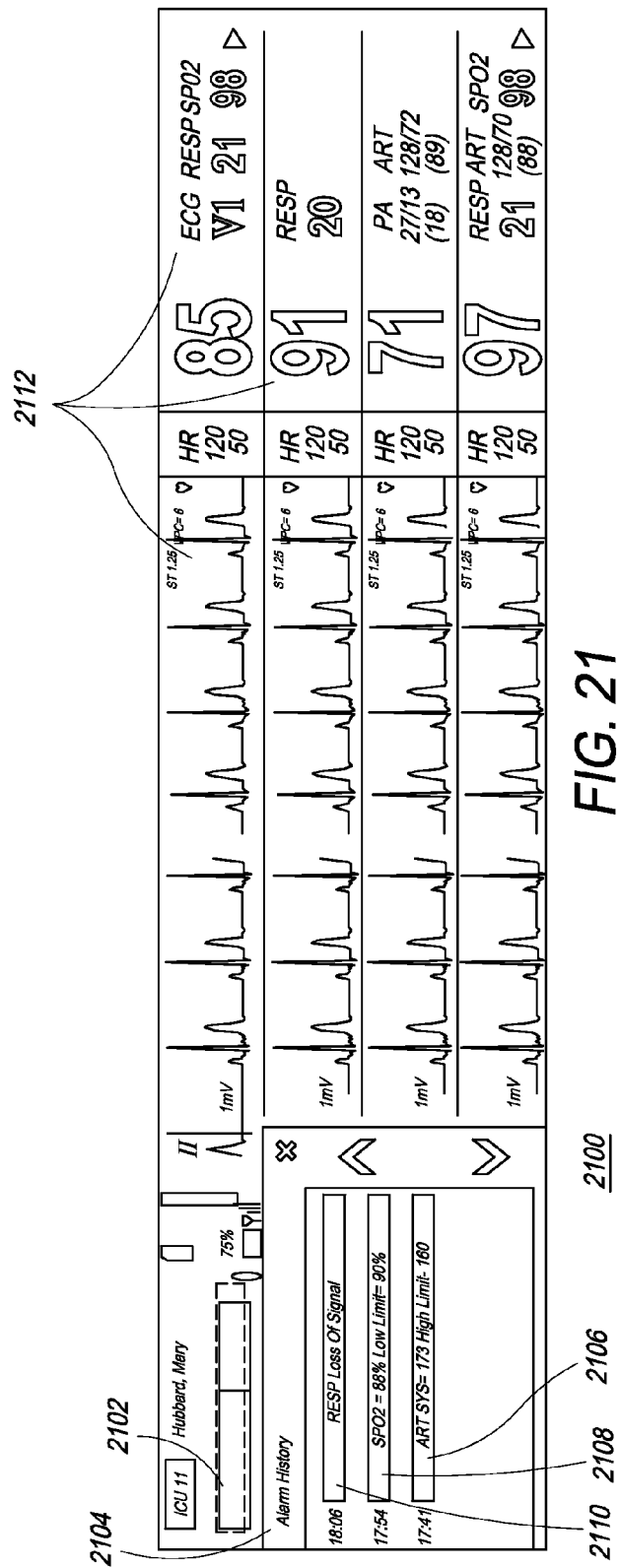
FIG. 21 is an illustration of one embodiment of a graphical user interface showing alarm events, in greater detail.

FIG. 21 is an illustration of one embodiment of a graphical user interface 2100 showing the alarm history bar and alarm events in greater detail. As shown in FIG. 21, alarm history bar 2102 further comprises window 2104, which is employed to provide a description for each alarm event in alarm history bar 2102. Thus, simultaneously referring to FIGS. 20 and 21, alarm events 2004, 2006 and 2008 correspond to alarm events for parameter values of ART SYS 2106, SpO₂ 2108 and RESP (respiration) 2110, respectively. Along with the values that triggered the alarm and the time of each alarm, the corresponding low and high threshold limits for each parameter in alarm are also displayed in the alarm descriptions 2106, 2108, and 2110. The remainder of interface screen 2100 preferably displays the current readings 2112 for various parameters.

The abovementioned method of highlighting alarms is particularly advantageous over existing and conventionally used latching alarms. Latching alarms are conventionally employed to remind clinicians of recent past alarms. Latching alarms can be very annoying and not necessarily a well accepted clinical solution, as they lead to more noise pollution in the intensive care and lessened sensitivity to alarm recognition. This method of presenting alarms in the present invention provides the requisite information quickly and enables efficient access to the data necessary to make a clinical decision.

The abovementioned embodiments are enabled by a software implementation of a human interface design to manage and display clinical history for a variety of patient monitored parameters. This design provides an easy to use process for formatting tables and graphs without need of formal instruction or lengthy operational manuals thus allowing for improved work flow. The tables and graphs can be customized for specialty care areas, physician preference, nursing preference, protocol management or research. Further, data presentation is exportable for research and teaching purposes. The system is easy to use and helps to rapidly visualize patient changes and review treatment plans accordingly.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A system for monitoring a plurality of physiological parameters of an individual using a plurality of physiological sensors, comprising:
   (a) a processor in data communication with a memory, wherein said memory stores physiological parameter data obtained from the plurality of sensors and wherein the processor executes a plurality of instructions to generate an interactive user interface based upon said physiological parameter data, said interactive user interface comprising:
      1. a first region having a plurality of icons, wherein each icon graphically represents a selectable graphical user interface view;
      2. a second region having a first interface and a second interface, wherein the first interface comprises a customizable table of measured values of physiological parameters presented in accordance with a time of measurement and wherein the second interface has a customizable graph of the measured values of physiological parameters presented in accordance with the time of measurement, wherein the first and second interfaces are displayed alternatively and not concurrently, and wherein the measured values of physiological parameters include heart rate, pulse rate, blood oxygen saturation level (SpO₂), and body temperature;
      3. a third region having at least one interface, wherein the at least one interface comprises a customizable graph of at least one measured value of at least one physiological parameter;
      4. a fourth region comprising a horizontally disposed timebar that defines said time of measurement and that, when slid horizontally, customizes the time period for display, wherein said interactive user interface displays each of said first, second, third, and fourth regions concurrently; and
   (b) a display unit coupled to said processor for visually displaying said user interface in accordance with the executed plurality of instructions.

2. The system of claim 1, wherein said physiological parameters further comprise ECG, blood oxygen saturation level (SpO₂), respiratory rate, blood glucose level, and blood pressure.

3. The system of claim 1 wherein said first region further comprises a menu having at least one button.

4. The system of claim 3 wherein the at least one button comprises at least one of a bedside icon, a waveform icon, an arrhythmia icon, an alarms icon, a saved events icon, a 12-lead icon, a trends icon, or a print jobs icon.

5. The system of claim 1 wherein the first region further comprises a patient name area.

6. The system of claim 1 wherein the second region further comprises a third alternative interface, wherein the third alternative interface is used for defining search parameters and wherein the first, second, and third interfaces are displayed alternatively and not concurrently.

7. The system of claim 6 wherein the second region has a fourth interface, wherein the fourth alternative interface is used for displaying defined search parameter data and wherein the first, second, third, and fourth interfaces are displayed alternatively and not concurrently.

8. The system of claim 7 wherein the second region has a fifth interface, wherein the fifth alternative interface is used for displaying banded graphs based on measured parameter data and wherein the first, second, third, fourth and fifth interfaces are displayed alternatively and not concurrently.

9. The system of claim 1 wherein the customizable graph presents, along a unified timeline, measured values for more than one physiological parameter.

10. A method for monitoring a plurality of physiological parameters of an individual using a plurality of physiological sensors, comprising:
   (a) receiving data on said physiological parameters;
   (b) processing said data on said physiological parameters to form a user interface, said user interface comprising:
      1. a first region having a plurality of icons, wherein each icon graphically represents a selectable graphical user interface view;
      2. a second region having first interface and a second interface, wherein the first interface comprises a customizable table of measured values of physiological parameters presented in accordance with a time of measurement, wherein the second interface has a customizable graph of measured values of physiological parameters presented in accordance with the time of measurement, wherein the first interface and second interface are displayed alternatively and not concurrently, and wherein the measured values of physiological parameters include heart rate, pulse rate, blood oxygen saturation level (SpO$_2$), and body temperature;

3. a third region having at least one interface, wherein the at least one interface comprises a customizable graph of at least one measured value of at least one physiological parameter;

4. a fourth region comprising a horizontally disposed timebar that defines said time of measurement and that, when slid horizontally, customizes the time period for display, wherein said interactive user interface displays each of said first, second, third, and fourth regions concurrently; and (c) visually displaying said user interface.

11. The method of claim 10, wherein said physiological parameters further comprise ECG, respiratory rate, blood glucose level, and blood pressure.

12. The method of claim 10 wherein said first region further comprises a menu having at least one button.

13. The method of claim 12 wherein the at least one button comprises at least one of a bedside icon, a waveform icon, an arrhythmia icon, an alarms icon, a saved events icon, a 12-lead icon, a trends icon, or a print jobs icon.

14. The method of claim 10 wherein the first region further comprises a patient name area.

15. The method of claim 10 wherein the second region has a third interface, wherein the third alternative interface is used for defining search parameters and wherein the first, second, and third interfaces are displayed alternatively and not concurrently.

16. The method of claim 15 wherein the second region has a fourth interface, wherein the fourth alternative interface is used for displaying defined search parameter data and wherein the first, second, third, and fourth interfaces are displayed alternatively and not concurrently.

17. The method of claim 16 wherein the second region has a fifth interface, wherein the fifth alternative interface is used for displaying banded graphs based on measured parameter data and wherein the first, second, third, fourth and fifth interfaces are displayed alternatively and not concurrently.

18. The method of claim 1 wherein the customizable graph presents, along a unified timeline, measured values for more than one physiological parameter.

* * * * *